US012144505B2

(12) United States Patent
Lamps et al.

(10) Patent No.: US 12,144,505 B2
(45) Date of Patent: Nov. 19, 2024

(54) ABDOMINAL APPROXIMATION DEVICE AND METHOD

(71) Applicant: Absolutions Med, Inc., Mountain View, CA (US)

(72) Inventors: Gregory Lamps, Smyrna, GA (US); Matthew Luis Rivera, Roswell, GA (US); Brad Richardson, Mountain View, CA (US); Daniel Jacobs, Mountain View, CA (US)

(73) Assignee: Absolutions Med, Inc., Mountain View, CA (US)

( * ) Notice: Subject to any disclaimer, the term of this patent is extended or adjusted under 35 U.S.C. 154(b) by 984 days.

(21) Appl. No.: 17/146,771

(22) Filed: Jan. 12, 2021

(65) Prior Publication Data

US 2021/0212685 A1 Jul. 15, 2021

Related U.S. Application Data

(60) Provisional application No. 62/976,261, filed on Feb. 13, 2020, provisional application No. 62/960,526, filed on Jan. 13, 2020.

(51) Int. Cl.
*A61B 17/08* (2006.01)
*A61B 17/02* (2006.01)

(52) U.S. Cl.
CPC .......... *A61B 17/08* (2013.01); *A61B 17/0281* (2013.01); *A61B 2017/081* (2013.01)

(58) Field of Classification Search
CPC . A61B 17/08; A61B 17/0281; A61B 17/0401; A61B 17/0466; A61B 2017/081;
(Continued)

(56) References Cited

U.S. PATENT DOCUMENTS 363,538 A 5/1887 Penny
3,698,395 A 10/1972 Hasson
(Continued)

FOREIGN PATENT DOCUMENTS

CN 204428091 U 7/2015
CN 106901789 6/2017
(Continued)

OTHER PUBLICATIONS

Fernandez, L., "Abdominal Closure," *Medscape*, https://emedicine.medscape.com/article/1961789-technique, Jun. 14, 2019.
(Continued)

*Primary Examiner* — Katherine H Schwiker

(74) *Attorney, Agent, or Firm* — Levine Bagade Han LLP

(57) ABSTRACT

Abdominal approximation devices and methods are described where one variation of the tissue securement assembly may generally include a fixation member having a length, a thickness control securement member which is adjustably securable along the length, and a frame which is adjustably securable to the thickness control securement member. The frame may have a relaxed configuration and a biasing configuration which imparts a biasing force against the thickness control securement member when in the biasing configuration such that the biasing force is applied at a distance from tissue to be approximated via the fixation member.

34 Claims, 28 Drawing Sheets

(58) Field of Classification Search
CPC ...... A61B 2017/0496; A61B 2017/086; A61B 2017/1142
See application file for complete search history.

(56) References Cited

U.S. PATENT DOCUMENTS

| | | | |
|---|---|---|---|
| 3,926,193 | A | 12/1975 | Hasson |
| 3,986,493 | A | 10/1976 | Hendren |
| 4,060,089 | A | 11/1977 | Noiles |
| 4,162,678 | A | 7/1979 | Fedotov et al. |
| 4,306,570 | A | 12/1981 | Matthews |
| 4,430,998 | A | 2/1984 | Harvey et al. |
| 4,539,990 | A | 9/1985 | Stivala |
| 4,548,202 | A | 10/1985 | Duncan |
| 4,610,250 | A | 9/1986 | Green |
| 4,667,674 | A | 5/1987 | Korthoff et al. |
| 4,805,617 | A | 2/1989 | Bedi et al. |
| 4,950,284 | A | 8/1990 | Green et al. |
| 5,234,462 | A | 8/1993 | Pavletic |
| 5,258,012 | A | 11/1993 | Luscombe et al. |
| 5,263,971 | A | 11/1993 | Hirshowitz et al. |
| 5,293,881 | A | 3/1994 | Green et al. |
| 5,358,510 | A | 10/1994 | Luscombe et al. |
| 5,534,010 | A | 7/1996 | Peterson |
| 5,662,649 | A | 9/1997 | Huebner |
| 5,800,436 | A | 9/1998 | Lerch |
| 5,893,855 | A * | 4/1999 | Jacobs ............... A61B 17/0684 606/213 |
| 5,916,224 | A | 6/1999 | Esplin |
| 6,050,988 | A | 4/2000 | Zuck |
| 6,485,503 | B2 | 11/2002 | Jacobs et al. |
| 6,645,226 | B1 | 11/2003 | Jacobs et al. |
| 6,730,014 | B2 | 5/2004 | Wilk |
| 6,893,452 | B2 | 5/2005 | Jacobs |
| 6,991,643 | B2 | 1/2006 | Saadat |
| 7,156,862 | B2 | 1/2007 | Jacobs et al. |
| 7,172,615 | B2 | 2/2007 | Morriss et al. |
| 7,238,188 | B2 | 7/2007 | Nesper et al. |
| 7,361,185 | B2 | 4/2008 | O'Malley et al. |
| 7,445,010 | B2 | 11/2008 | Kugler et al. |
| 7,510,566 | B2 | 3/2009 | Jacobs et al. |
| 7,972,347 | B2 | 7/2011 | Garvin et al. |
| 8,114,101 | B2 | 2/2012 | Criscuolo et al. |
| 8,114,124 | B2 | 2/2012 | Buckman et al. |
| 8,323,313 | B1 | 12/2012 | Belson et al. |
| 8,663,275 | B2 | 3/2014 | O'Malley et al. |
| 8,764,778 | B2 | 7/2014 | Yeretsian |
| 8,801,754 | B2 | 8/2014 | Walshe |
| 8,915,942 | B2 | 12/2014 | Zhang |
| 9,149,297 | B2 | 10/2015 | Kirschman |
| 9,179,914 | B2 | 11/2015 | Belson et al. |
| 9,198,689 | B2 | 12/2015 | Dale et al. |
| 9,271,730 | B2 | 3/2016 | Fleischmann |
| 9,414,840 | B2 | 8/2016 | Fleischmann |
| 9,474,529 | B2 | 10/2016 | Belson et al. |
| 9,486,217 | B2 | 11/2016 | Moustafa |
| 9,554,799 | B2 | 1/2017 | Belson et al. |
| 9,662,112 | B2 | 5/2017 | Nash et al. |
| 9,693,776 | B1 | 7/2017 | Moustafa |
| 10,010,710 | B2 | 7/2018 | Belson et al. |
| 10,022,216 | B2 | 7/2018 | Ricci et al. |
| 10,456,136 | B2 | 10/2019 | Belson et al. |
| 11,071,547 | B2 | 7/2021 | Jacobs et al. |
| 11,344,398 | B2 | 5/2022 | Lamps et al. |
| 11,382,610 | B2 | 7/2022 | Lamps et al. |
| 11,877,920 | B2 | 1/2024 | Lamps et al. |
| 2003/0092969 | A1 * | 5/2003 | O'Malley ............... A61B 17/02 600/216 |
| 2003/0125743 | A1 | 7/2003 | Roman et al. |
| 2004/0044364 | A1 | 3/2004 | Devries et al. |
| 2004/0059358 | A1 | 3/2004 | Kortenbach et al. |
| 2004/0102779 | A1 | 5/2004 | Nesper et al. |
| 2004/0138683 | A1 | 7/2004 | Shelton et al. |
| 2004/0267300 | A1 | 12/2004 | Mace |
| 2004/0267309 | A1 | 12/2004 | Garvin |
| 2005/0197699 | A1 | 9/2005 | Jacobs et al. |
| 2006/0058842 | A1 * | 3/2006 | Wilke ............... A61B 17/0466 606/213 |
| 2006/0074448 | A1 | 4/2006 | Harrison et al. |
| 2006/0167482 | A1 | 7/2006 | Swain et al. |
| 2006/0247637 | A1 | 11/2006 | Colleran et al. |
| 2007/0123914 | A1 | 5/2007 | Lizardi et al. |
| 2008/0046008 | A1 | 2/2008 | Smith et al. |
| 2008/0234698 | A1 | 9/2008 | Oostman et al. |
| 2008/0262540 | A1 | 10/2008 | Bangera et al. |
| 2008/0262543 | A1 | 10/2008 | Bangera et al. |
| 2009/0163937 | A1 | 6/2009 | Kassab et al. |
| 2009/0234358 | A1 | 9/2009 | Morales et al. |
| 2010/0069932 | A1 | 3/2010 | D'Arcangelo et al. |
| 2011/0092993 | A1 | 4/2011 | Jacobs |
| 2012/0029539 | A1 | 2/2012 | Dennis |
| 2012/0130374 | A1 | 5/2012 | Bouduban et al. |
| 2012/0221044 | A1 | 8/2012 | Archibald et al. |
| 2013/0197577 | A1 | 8/2013 | Wolf et al. |
| 2013/0325046 | A1 | 12/2013 | Terwiske et al. |
| 2014/0094830 | A1 | 4/2014 | Sargeant et al. |
| 2014/0214078 | A1 | 7/2014 | Moustafa |
| 2014/0316323 | A1 | 10/2014 | Kanevsky et al. |
| 2016/0095591 | A1 | 4/2016 | Smith et al. |
| 2016/0113650 | A1 | 4/2016 | Lord et al. |
| 2016/0249924 | A1 | 9/2016 | Belson et al. |
| 2016/0310140 | A1 | 10/2016 | Belson et al. |
| 2017/0156847 | A1 | 6/2017 | Ricci et al. |
| 2017/0290580 | A1 | 10/2017 | Soltanian |
| 2017/0296161 | A1 | 10/2017 | Marshall |
| 2017/0325935 | A1 | 11/2017 | Fuller et al. |
| 2018/0036006 | A1 | 2/2018 | De Rezende Neto |
| 2018/0078253 | A1 | 3/2018 | Kubiak et al. |
| 2018/0078257 | A1 | 3/2018 | Buttar |
| 2018/0116778 | A1 | 5/2018 | Chin et al. |
| 2018/0200042 | A1 | 7/2018 | Kubiak et al. |
| 2018/0214148 | A1 | 8/2018 | Christiansen et al. |
| 2018/0250121 | A1 | 9/2018 | Kubiak et al. |
| 2019/0038274 | A1 | 2/2019 | Quintero et al. |
| 2019/0167260 | A1 | 6/2019 | Levinson et al. |
| 2020/0078018 | A1 | 3/2020 | Jacobs et al. |
| 2020/0107826 | A1 | 4/2020 | Kojouri et al. |
| 2020/0323614 | A1 | 10/2020 | Lamps et al. |
| 2021/0128151 | A1 | 5/2021 | Jacobs et al. |
| 2021/0236126 | A1 * | 8/2021 | Newell ............... A61B 17/08 |
| 2022/0142761 | A1 | 5/2022 | Lamps et al. |
| 2022/0287703 | A1 | 9/2022 | Kojouri et al. |
| 2023/0022119 | A1 | 1/2023 | Lamps et al. |
| 2023/0047828 | A1 | 2/2023 | Lamps et al. |
| 2024/0099823 | A1 | 3/2024 | Lamps et al. |

FOREIGN PATENT DOCUMENTS

| | | |
|---|---|---|
| CN | 107822682 | 3/2018 |
| JP | 2006-500090 | 10/2006 |
| JP | 2017-531538 | 10/2017 |
| WO | WO 2001/067944 | 9/2001 |
| WO | WO 2003/039620 | 5/2003 |
| WO | WO 2017/000758 | 1/2017 |
| WO | WO 2018/031509 | 2/2018 |
| WO | WO 2018/069543 | 4/2018 |
| WO | WO 2020/055757 | 3/2020 |
| WO | WO 2020/072259 | 4/2020 |
| WO | WO 2020/210463 | 10/2020 |
| WO | WO 2021/146165 | 7/2021 |
| WO | WO 2021/183787 | 9/2021 |
| WO | WO 2023/004217 | 1/2023 |
| WO | WO 2023/023486 | 2/2023 |
| WO | WO 2024/030688 | 2/2024 |

OTHER PUBLICATIONS

Lorenz® Plating System LactoSorb® RapidFlap™ LS brochure, 4 pages, Oct. 1, 2008.

* cited by examiner

ABDOMINAL APPROXIMATION DEVICE AND METHOD

CROSS-REFERENCE TO RELATED APPLICATIONS

This application claims the benefit of priority to U.S. Prov. App. 62/960,526 filed Jan. 13, 2020 and U.S. Prov. App. 62/976,261 filed Feb. 13, 2020, each of which is incorporated herein by reference in its entirety.

FIELD OF THE INVENTION

The present invention relates to methods and apparatuses for approximating tissue regions. More particularly, the present invention relates to methods and apparatuses for approximating edges of a wound towards one another while allowing the wound itself to remain either completely unobstructed or easily accessed for management.

BACKGROUND OF THE INVENTION

Abdominal surgeons often encounter difficult abdominal closures after trauma or extensive abdominal surgery. In such situations, swelling of the abdominal contents increases the intra-abdominal volume such that closure of the abdominal wall is either impossible or must be performed under excessively high tension. Soft tissues, however, cannot tolerate high tension, and typically fails to remain approximated under such stresses, thus leading to failure of the closure and a future ventral hernia. Alternatively, excessive tension can lead to high intra-abdominal pressures, causing potentially fatal abdominal compartment syndrome.

To avoid the complications and risks associated with excessively tight abdominal closure, the abdomen may be left open. In this setting, either a delayed closure is performed after abdominal edema subsides or a skin graft may be placed over the open abdominal wound, leaving a gaping structural defect for the patient.

An approach to expediting delayed closure of the edematous abdomen is the ABRA® Abdominal Wall Closure System (Dynamic Tissue Systems®, Southmedic, Inc., Ontario, Canada), which entails multiple elastic members crossing an open wound and applying tension that can be adjusted regularly by the surgeon in order to advance the fascial edges to their normal anterior, midline position.

Although a step forward, the ABRA® device suffers from its placement within the abdomen, posing a threat to underlying intestinal structures, much like retention sutures. The device includes a large, protective silastic sheet to separate viscera from the elastic bands, but the silastic sheet, itself, has edges sitting within the abdomen that pose a risk to intra-abdominal contents. The device also impedes access to the abdominal cavity necessary for care. It is also not clear how the device would work in the absence of an open abdominal wound (elective hernia closure), or in support of a difficult closure (fascia is apposed but under high tension and high risk of failure) where it would be impossible to later remove the protective silastic sheet without additional surgery.

SUMMARY OF THE INVENTION

In abdominal incisions or wounds for which high tension precludes safe primary closure, expedited delayed closure may be achieved with devices placed on each side of the abdominal opening in a manner that gradually approximates the edges for later repair under reduced tension, all the while avoiding risks of intra-abdominal placement, yet enabling rapid access to intra-abdominal contents for serial interventions.

Such devices may be attached to the abdominal wall and, rather than spanning the incision or wound to apply tension in the direction of the midline, apply force from a frame or mechanism located peripheral to the incision. In some cases, the force that the peripheral frame or mechanism applies may be inadequate by itself to approximate the edges of the wound and additional elastic members or components creating medial force may be placed across the incision.

Another indication for such devices is to temporarily support a primary or delayed closure during an initial healing phase such that a subsequent dehiscence or hernia is less likely to occur.

The ideal corrective approach to the open abdomen would dynamically (e.g., non-rigid force) approximate or support abdominal wall components while:
  a. Maintaining integrity of the abdominal wall structures (in contradistinction to component separation),
  b. Avoiding spanning materials (at or below the plane of the skin) across the incision or wound so as to preclude device related injury to the underlying intestine or viscera,
  c. Avoiding functional obstruction of access to the incision to enable care of the abdominal wound, and
  d. Be easily removed in the office or operating room when no longer necessary.

The invention generally entails a first fixation member such as an elongate pin or structural member that may be affixed at a first location through the abdominal wall near or at a first edge of an incision or wound. The fixation member may incorporate a backing or shoulder member which may provide a fixed or collapsible anchor to maintain the fixation member in place within the tissue and prevent or inhibit the member from being pulled out of the tissue. An additional thickness control securement member may be arranged on or incorporated into the fixation member to hold the fixation member in place relative to the surface of the tissue (preventing the fixation member from penetrating deeper into the abdomen). A second fixation member, which may also be an elongate pin or structural member, may be affixed at a second location through the abdominal wall near or at a second edge of the incision or wound opposite the first location. The second fixation member may similarly incorporate an anchoring member and thickness control securement member. The anchor and thickness control securement which secure the first and second fixation members to the tissue may be various mechanisms such as disks, medical balloons, screws, pins, hooks, compressive mechanism, etc. and as further described in detail below.

A frame may be arranged around the incision or wound in the area where the fixation members are affixed to the tissue. This frame may be rigid or flexible. The frame may have one or more joints that allow it to be adjusted to approximately follow the natural curves of the abdomen or to allow for patient motion. Said adjustment may be made manually or may be accomplished automatically. In one embodiment, a biasing member connects the frame to each fixation member and applies a force to move the fixation member towards the open wound. This force applied to opposing fixation members translates to the tissues to dynamically approximate the edges, thus closing the wound over time. As no guiding or tensioning members cross within the open wound in contact with tissue, the risk of injury to the viscera is greatly reduced. In addition, medical caregivers have easy access to the abdominal wound to change dressings, perform washouts, etc.

Rather than a biasing member connecting the frame to each fixation member to apply force to close the wound, alternatively, the frame itself may provide the biasing force. This is accomplished by constructing the frame from a flexible rod or other structure that acts as a spring and pushes against or pulls on the tissue fixation members either directly or through a connecting rigid or semi-rigid body. The flexible rod or other structure may be a monolithic piece or be constructed from more than one piece to give a similar effect.

The force applied to the abdominal wall structures may be dynamic, using various biasing mechanisms as described in further detail herein (such as springs, elastic bands, gas shocks, ratcheting mechanism, etc.) where the application of the force is removed from or remote to or at a distance from where the first and second fixation members are secured to the tissue outside of the abdominal wall plane. The force may be translated through the tissue securement assembly to the underlying tissue. To ensure the device applies force to the abdominal wall while maintaining sufficient kinematic restraint, moment resisting features such as bars, rail mounted linear bearings, washers mounted anterior to the skin, multi-bar linkages, etc. may be utilized as described in further detail herein.

This enables the first and second fixation members to approximate the underlying tissue edges towards one another without the first and second fixation members collapsing onto or excessively leaning into the skin surface or wound, which would create risk of tissue injury. The force applied to the fixation members as described herein may be compressive, tensile, torsion, or other types of force for approximating the tissue.

Each of the biasing members may be slidingly secured on the frame to better align the force with each tissue fixation member. Accordingly, provision may be made to allow for the biasing member to be set at a fixed angle relative to the frame. In another embodiment, the angle between the biasing member and frame may be free to rotate, have limited compliance, or be adjustable to various angles or positions.

One variation of the tissue securement assembly may generally comprise a first fixation member having a first length, an anchor positionable near or at a proximal end (e.g., deep to the abdominal wall) of the first length, and a thickness control securement which is adjustably securable along a distal portion of the first length (e.g., above the surface of the abdominal wall skin), wherein the thickness control securement has a provision for attaching directly or indirectly to a frame having an elongate length exterior to the margin of the wound.

Another variation of the tissue securement assembly may generally comprise a first fixation member having a first length, an anchor positionable near or at a proximal end (e.g., deep to the abdominal wall) of the first length, a thickness control securement which is adjustably securable along a distal portion of the first length (e.g., above the surface of the abdominal wall skin), and a frame securement support located more distally than the thickness control securement, wherein the frame securement support has a provision for attaching directly or indirectly to a frame having an elongate length exterior to the margin of the wound. As described, the biasing force is applied at a distance removed or remote from the surface of the wound or incision and the force is then transmitted directly to the underlying tissue via the fixation members. Accordingly, the height of the frame securement support may be adjusted to a desired height above the tissue.

Another variation of the apparatus may utilize an inflatable or expandable anchor to maintain a position of the fixation member relative to the tissue. An inflatable balloon or otherwise expandable member may be advanced through or along the fixation member for securing the apparatus to the tissue. In this variation, the balloon may have an elongate shaft with a valve member positioned at or near the opposite end of the device (from the balloon).

One method of approximating tissues of an open abdominal wall may generally comprise securing a first fixation member at a first tissue region in proximity to a first edge of a wound or incision, securing a second fixation member at a second tissue region in proximity to a second edge of the wound or incision opposite the first tissue region, coupling the first fixation member and the second fixation member to one another indirectly via a frame which essentially encompasses the width and breadth of the wound or incision, wherein biasing members connect each fixation member to the frame and apply a force to each fixation member moving the margins of the wound or incision towards each other. In a variation of this method, the frame itself provides the biasing force to fixation members.

In another variation, the frame consists of a series of linkages connecting each fixation member with a biasing member and arranged to pull the fixation members on each side of the wound towards their respective neighboring fixation members on the same side of the wound. This approximating force of the fixation members on the side of the wound towards each other tends to shorten the distance between neighboring fixation members which shortens the overall length of the curve of the wound. As the length of the curve shortens, the curve tends to become linear and comes into apposition with the opposing side which is undergoing the same forces.

One variation of the tissue securement assembly may generally comprise a fixation member having a length, a thickness control securement member which is adjustably securable along the length, and a frame which is adjustably securable to the thickness control securement member. The frame may have a relaxed configuration and a biasing configuration which imparts a biasing force against the thickness control securement member when in the biasing configuration such that the biasing force is applied at a distance from tissue to be approximated via the fixation member.

Another variation of the tissue securement assembly may generally comprise a first fixation member having a first length, a first thickness control securement member which is adjustably securable along the first length, a second fixation member having a second length, a second thickness control securement member which is adjustably securable along the second length, and a frame which is adjustably securable between the first thickness control securement member and the second thickness control securement member such that the frame encompasses a wound or incision within the frame. The frame may have a relaxed configuration and a biasing configuration which imparts a biasing force between the first and second thickness control securement members when in the biasing configuration such that the biasing force is applied at a distance from tissue to be approximated via the fixation member.

One variation of a method for approximating tissue may generally comprise securing a first fixation member having a first length into a first region of tissue in proximity to a wound or incision, adjustably securing a first thickness control securement member along the first length, securing a second fixation member having a second length into a second region of tissue in proximity to the wound or incision and opposite to the first fixation member, adjustably securing a second thickness control securement member along the second length, adjustably positioning a frame between the first thickness control securement member and the second thickness control securement member such that the frame encompasses the wound or incision within the frame, and imparting a biasing force between the first and second thickness control securement members via the frame.

Another variation of the tissue securement assembly may generally comprise a fixation member having a length, a thickness control securement member which is adjustably securable along the length, a frame which is adjustably positionable relative to a wound or incision such that the frame at least partially surrounds the wound or incision, and a biasing member coupled between the frame and the thickness control securement member such that the biasing member provides a biasing force against the thickness control securement member at a distance from the wound or incision to be approximated.

Another variation of the method for approximating tissue may generally comprise securing a first fixation member having a first length into a first region of tissue in proximity to a wound or incision, adjustably securing a first thickness control securement member along the first length, securing a second fixation member having a second length into a second region of tissue in proximity to the wound or incision and opposite to the first fixation member, adjustably securing a second thickness control securement member along the second length, adjustably positioning a frame between the first thickness control securement member and the second thickness control securement member such that the frame at least partially encompasses the wound or incision within the frame, imparting a first biasing force via a first biasing member between the first thickness control securement member and a first portion of the frame, and imparting a second biasing force via a second biasing member between the second thickness control securement member and a second portion of the frame opposite to the first thickness control securement member such that the first and second biasing forces are directed towards one another.

DETAILED DESCRIPTION OF THE INVENTION

Figure 1A:
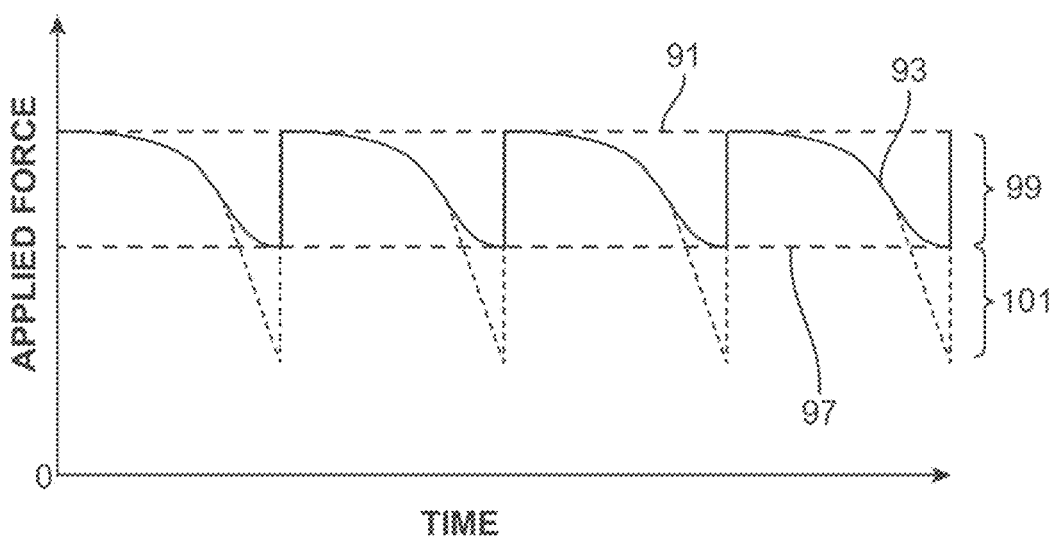
FIG. 1A shows an example of how the dynamic force may be applied to the tissue by the apparatus.

In the scenario where the surgeon is able to close the abdomen but perceives a high risk of dehiscence, the devices described herein may be attached to the abdomen, encompassing the incision or wound, but the force applied by the device to approximate the edges of tissue 608 towards one another may be applied in a manner which reduces tension on the sutures (or other closure device), essentially functioning as an external, dynamic retention suture support mechanism. The devices described herein may also be utilized to apply force to close an incision or wound and allow for sutures or other closure devices to be utilized after the subject device has approximated the edges of the wound or incision.

One example of gradual wound approximation allows for the repair of abdominal wall defects by applying dynamic forces outside of the abdominal cavity and transferring these dynamic forces to the tissues 608. This allows for gradual approximation of the abdominal wall components to their normal anatomic positions without the presence of materials spanning the wound within the abdomen, thus reducing the possibility of injury to intra-abdominal organs. It can be used in acute, open wounds (resulting, for example, from trauma, pancreatitis, etc.) or in high-risk surgical closures to support the midline until intra-abdominal pressures return to near normal or until healing or partial healing has occurred, thus reducing future ventral hernias. In certain circumstances, the apparatus could be used to facilitate elective ventral defect closures in which there is no open wound, but fascial edges are too far apart for simple closure.

Generally, a first fixation member 210 such as an elongate pin or structural member may be affixed at a first location through the abdominal wall such as a first rectus abdominis region near or at a first edge of an incision or wound. The fixation member 210 may incorporate an anchor member which may provide support to maintain the fixation member 210 in place within the tissue 608 and prevent or inhibit the member from being pulled out of the tissue 608. A thickness control securement 212 member may be arranged on, coupled to, or incorporated into the fixation member 210 to hold the fixation member 210 in place relative to the surface of the tissue 608 (preventing the fixation member 210 from penetrating deeper into the abdomen). Together the fixation member 210, anchor member, and thickness control securement 212 member in one variation form a tissue securement assembly 502. A second tissue securement assembly 502 may be affixed at a second location through the abdominal wall through a second rectus abdominis region near or at a second edge of the incision or wound opposite, or nearly opposite, the first location. The anchor 258 and thickness control securement 212 which secure the first and second fixation members 210 to the tissue 608 may be various mechanisms such as disks, medical balloons, screws, pins, hooks, compressive mechanism, etc. and as further described in detail below.

A frame 500 may be adjustably securable to the first tissue securement assembly 502 at a first connection and may also be adjustably securable to the second tissue securement assembly 502 at a second connection. The frame 500 may have a length and width sufficient to encompass the incision or wound while maintaining securement to the first and second fixation members 210 in a transverse, non-parallel (to the incision), or angled orientation. Furthermore, the frame 500 may be configured to provide a force to the first and second tissue securement assemblies either simultaneously or singularly to a single tissue securement assembly 502 while maintaining the transverse, non-parallel, or angled orientation. The force may be applied as an essentially constant force to the abdominal wall structures using various biasing mechanisms, as described in further detail herein (such as springs, elastic bands, ratcheting mechanism, etc.) where the application of the force is removed or remote or at a distance from where the first and second tissue securement assemblies are secured to the tissue 608 and is therefore located outside of the abdominal wall plane, for instance, 2 mm or greater above the surface of the tissues. To minimize the torsion applied to the tissue securement assemblies it may be preferable to avoid having the force applied at an excessively large distance from the surface of the tissues, for instance, 10 mm or less above the surface of the skin. The force may be transmitted through the tissue securement assemblies to the underlying tissue 608. Hence, the attachments may be moment-resisting to ensure that the apparatus has sufficient kinematic constraint. To ensure the device applies force to the abdominal wall while maintaining sufficient kinematic restraint, moment resisting features such as bars, rail mounted linear bearings, washers mounted anterior to the skin, multi-bar linkages, etc. may be utilized.

That is, the first and second tissue securement assemblies may be pushed or approximated towards one another via the application of force from the frame 500 while the orientation of the first and second tissue securement assemblies relative to the frame 500 remains unaltered. This enables the first and second tissue securement assemblies to approximate the tissue securement assemblies without collapsing onto the skin surface or wound. In some embodiments the force is not applied against the frame 500 but rather is applied directly by a flexible or elastic frame 500.

Apposition (or approximation) of the abdominal wall edges is achieved gradually by applying force via the first and second tissue securement assemblies located within the full thickness of the abdominal wall. When surgical apposition of the abdominal wall edges is accomplished using such a system, subsequent surgery is simplified since the abdominal wall tissues are now in their normal anatomic positions and relatively tension free.

Generally, for scenarios where the fascial defect is closed, the closure may be supported during the early post-operative period and the apparatus may be removed when it is no longer necessary. Such an apparatus might include a balloon anchor that can be deflated, allowing easy removal of the device when no longer necessary by deflating the balloon and extracting the device anteriorly. On the other hand, generally for scenarios where the fascial defect and skin are open, a procedure may be used to approximate the leading edges of the fascial tissue and skin together by utilizing the apparatus as further described herein. In such a scenario, a collapsible anchor 258 may not be necessary and the anchor 258 may thus be made from steel, titanium, or other rigid material which may be removed at a later time, such as the time of final fascial closure.

During the course of tissue approximation, as the tissue edges of the wound or incision are approximated towards one another, the tensioning force applied by tissue approximation devices will naturally drop towards net zero such as when equal to the resting and/or muscular plus elastic recoil of the tissues. In order to maintain a tensioning force imparted by the tissue approximation devices upon the tissue 608, the tissue approximation devices may be re-tensioned by one or more methods to maintain the desired tensile force upon the tissues.

In some embodiments, it may be desirable that the manner in which the force is applied to approximate the tissue edges of the wound or incision remains essentially constant or above intrinsic tissue recoil forces (non-equilibrating) during application of the force over the course of treatment. This may be accomplished by utilizing biasing mechanisms which continue to apply the force to the tissue securement assemblies and ultimately to the underlying secured tissues while exceeding the tissue recoil forces through various ranges of tissue edge approximation. Occasional adjustment or exchange of the biasing member 208 may allow for tension throughout the entire range of apposition distances.

Various examples of biasing mechanisms which may be incorporated with the devices and methods described herein are further disclosed in further detail in the following: U.S. Pub. 2020/0078018A1; U.S. Pub. 2020/0107826A1; U.S. Pub. 2020/0323614A1; and U.S. patent application Ser. No. 17/023,022 filed Sep. 16, 2020, each of which is incorporated herein by reference and for any purpose. Various combinations between different embodiments described in these references and the various features described herein are intended to be combined in any combination, as practicable.

An example is shown in the graph of FIG. 1A which illustrates how the applied tensioning force 93 using the devices herein may be applied such that the force remains either at an essentially constant level 91 or in a varying but non-equilibrating (above tissue recoil forces 97) manner where the apparatus may be adjusted as necessary to restore desired forces applied via the biasing mechanism. Although the applied force may decline over time or distance, since the biasing mechanism remains or is adjusted to maintain a force greater than tissue recoil forces, continuous gradual closure occurs rather than intermittent, stair-step tissue advancement seen with non-dynamic mechanisms or mechanisms with small dynamic ranges. As the tissue wound edges approximate, there remains a threshold level of force which may be applied to the tissue 608 in order to move the wound edges towards one another. An applied force below this threshold level may be ineffective or excessively prolonged in approximating the tissue edges as it does not adequately exceed tissue recoil forces. With the application of the appropriate biasing mechanism, the imparted approximating force range 99 which is effective in bringing the wound edges towards one another may be maintained either continuously or over a relatively longer period of time above the threshold level before falling below the threshold level where the applied force range 101 may become less or ineffective.

Figure 1B:
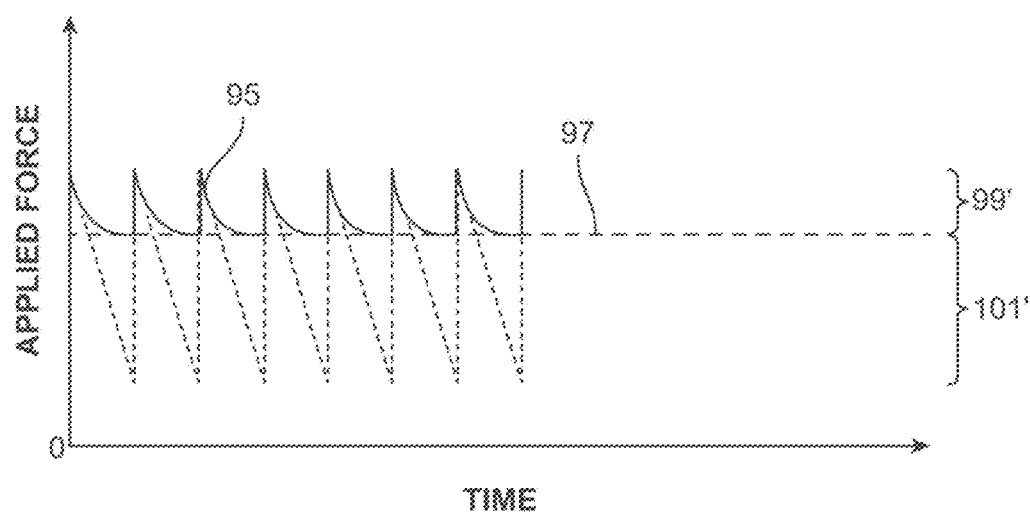
FIG. 1B shows an example for contrasting how a conventional tissue approximation device applies force to the tissue and requires frequent tightening to maintain the tissue approximation force on the tissue.

This is in contrast to the graph of FIG. 1B which illustrates how the tensioning force 95 using a conventional tissue approximation device such as sutures or screws will typically fall below the effective threshold level 97 (or that of the intrinsic recoil force of involved tissue) relatively quickly, thus creating durations wherein no apposition is occurring and/or requiring frequent re-tightening. This is due to the lack of a biasing mechanism which maintains the sutures or screws under an essentially constant, dynamic force. For example, a conical compression spring could be utilized via a spiral coil of spring wire whereby the variable spring rate per coil (due to varying pitch and diameter) allows the spring to have a relatively constant force over a range of compressions. By careful selection of pitches and diameters, the force within working ranges can be maintained at a level which is approximately constant.

The wide dynamic range of the tensioning device allows for smaller peaks and troughs of force. As such, the maximum amount of force applied by the biasing mechanism may be at a level which is relatively lower (e.g., 50% to 90% of conventional methods—145 g to 260 g) than the maximum amount of force applied by conventional tissue approximation devices, and thus results in greater comfort to the patient and lower risk of tissue injury. Such a biasing mechanism may apply an effective amount of approximating force for a relatively longer period of time (e.g., 50% to 100% longer 36 to 48 hours) when compared to the conventional tissue approximation devices, which frequently exit their dynamic range and need to be readjusted frequently.

In addition, a system of rigid members such as screws or sutures may fail to yield if tissue tension paroxysmally increases (for example if the patient coughs or moves) due to their unyielding mechanisms. Increases in tension or shear forces may thus result in pain or tearing of the tissue 608. On the other hand, the dynamic biasing forces of the described invention yield during increases in tissue tension due to the ability of opposing tissue securement assemblies to move relative to one another (towards or away from one another). This ability to move and adjust while still maintaining a biasing force on the tissue 608 may result in an alleviation of excessive imparted external forces and reduce pain and tissue damage.

All descriptions herein which refer to one pair of tissue securement assemblies being approximated towards each other can be understood to also encompass more than one pair of members being approximated and may furthermore encompass a situation in which tissue securement assemblies are not equally paired.

Figure 2:
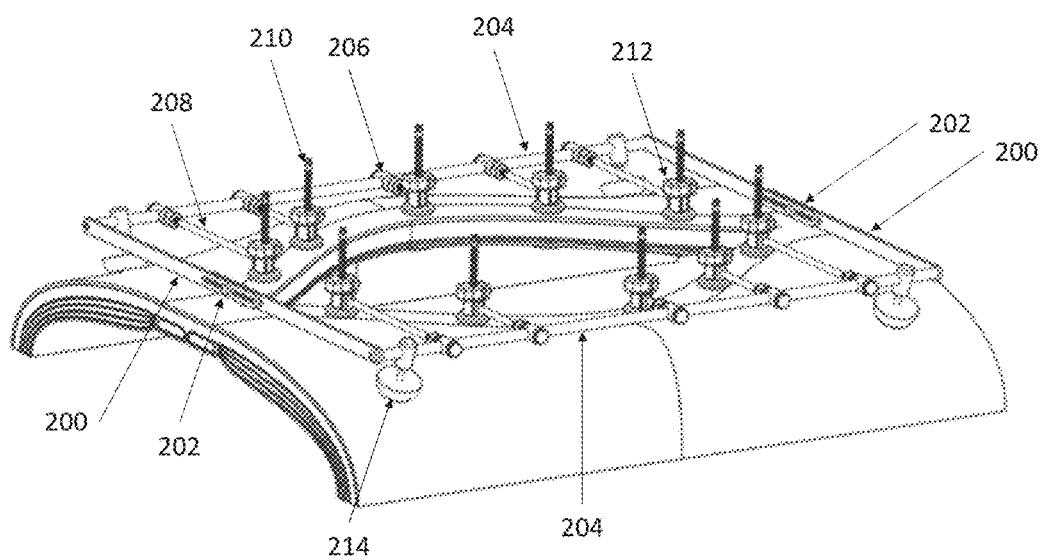
FIG. 2 shows an embodiment of a tissue approximation system which may utilize biasing members pushing against tissue securement assemblies and a rigid frame.
Figure 3A:
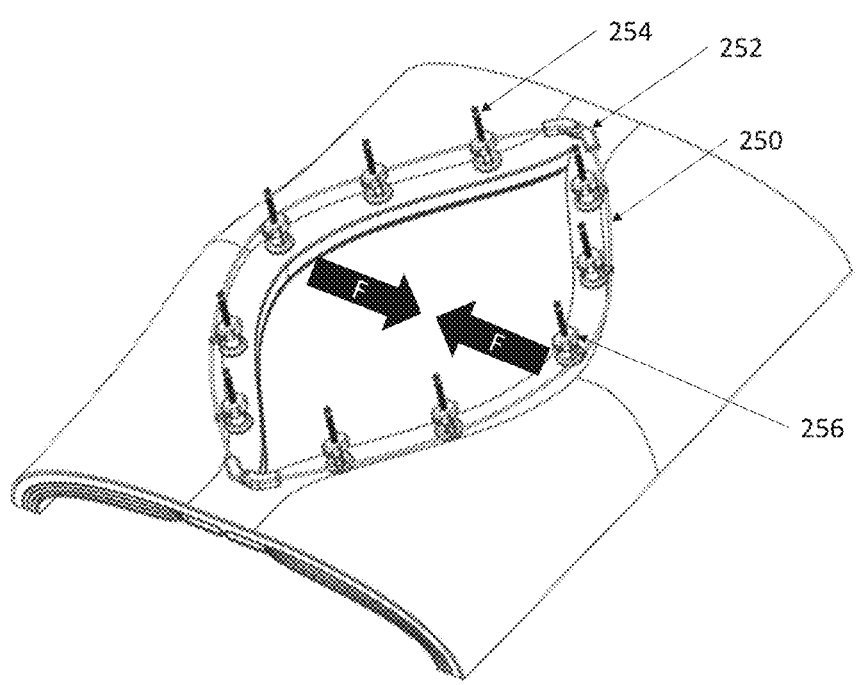
FIGS. 3A, 3B, and 3C show various views of an embodiment of a tissue approximation system which may utilize flexible spring members to impart forces to approximate the edges of a wound.
Figure 3B:
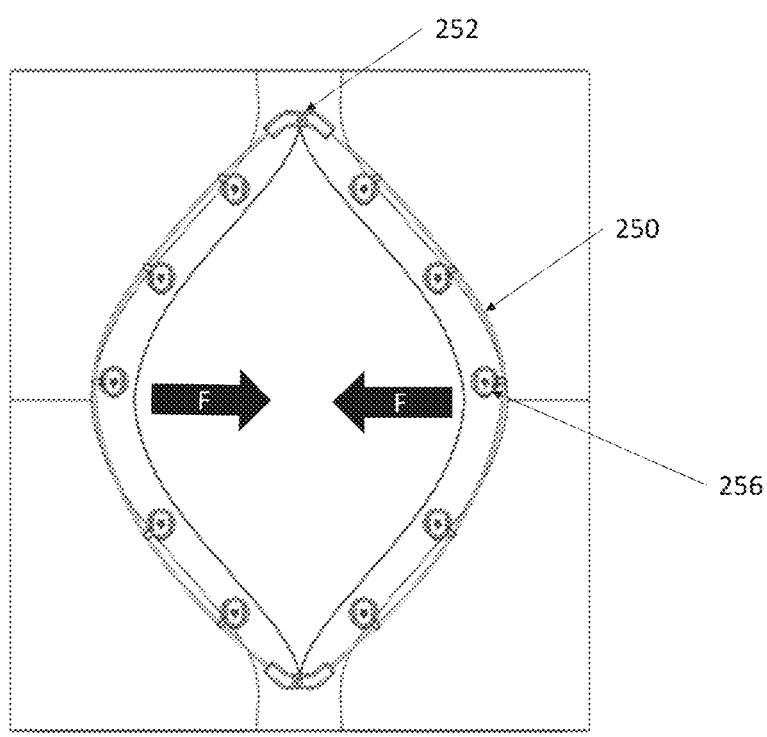
Figure 3C:
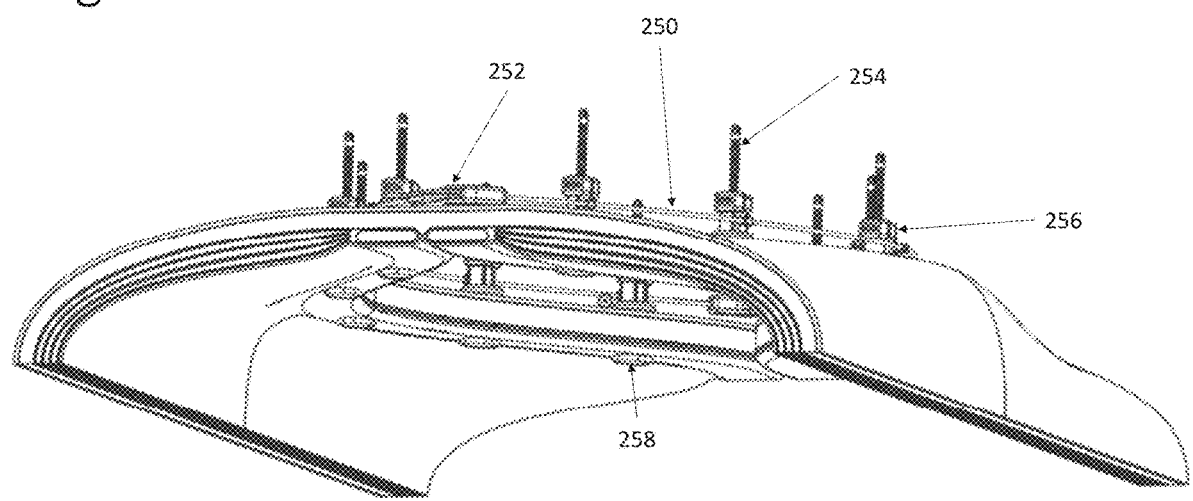
Figure 3D:
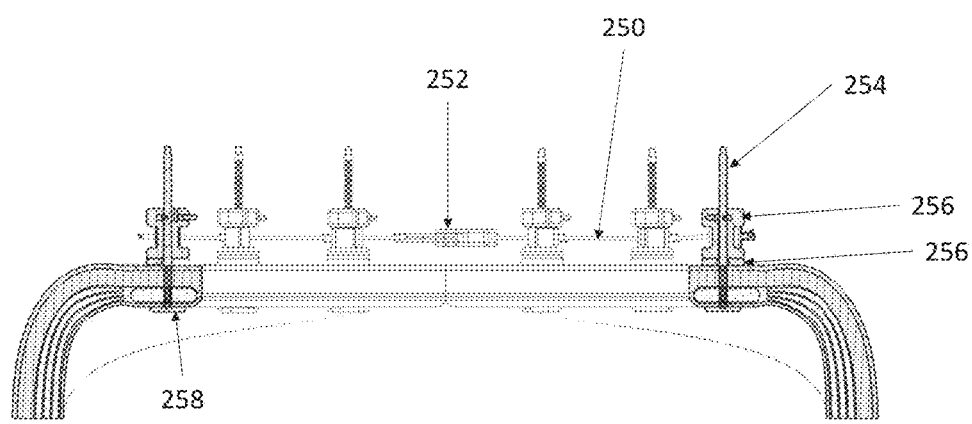
FIG. 3D shows a cross-sectional view of the tissue approximation apparatus illustrating how the fixation members may incorporate an anchor or shoulder, having a diameter which is larger than a diameter of the fixation members.

Turning to one variation of the apparatus, FIG. 2 shows an embodiment of a tissue approximation system that may utilize a first and second fixation member which may be secured at first and second respective locations on opposite sides of a wound or incision in proximity to the respective edges. The first and second fixation members 210 may be each inserted into the abdominal wall and secured in place in part or in combination by an anchor 258 which has threads or other features which engage with mating features of the fixation member 210 and a thickness control securement 212 through which the fixation member 210 may be slidingly insertable through and selectively secured to prevent further movement of the fixation member 210 relative to the thickness control securement 212.

The fixation members 210 or thickness control securements 212 may be connected to a rigid or an adjustable frame extending partially or entirely around the outside of the wound or incision by one or more biasing members 208. In this manner, the adjustable frame may be used as a base against which fixation members 210 may be driven towards the opposing edges of the wound or incision with the biasing members 208 applying a force to each of the respective tissue securement assemblies. The biasing member 208 may provide a dynamic force continuously above tissue recoil forces to each of the respective tissue securement assemblies, such that they are optimally moved towards the opposing fixation member 210 row attached to the opposite side of the frame or biasing member 208. For example, a force of 100 to 400 grams may be applied by the fixation members 210 and this in turn transmits force to the underlying tissue edges through the tissue securement assemblies to approximate the edges of the wound or incision while maintaining an orientation of the tissue securement assemblies relative to the underlying tissue 608.

Furthermore, the amount of force applied may be varied over the length of treatment. For instance, an initial force of, e.g., 150 to 300 grams, may be applied at the initial treatment when the fixation members 210 are first inserted within the tissue 608. After a period of time as the edges of the wound begin to approximate towards one another, the amount of force applied may be maintained at the same level or reduced by, e.g., 50%, by adjusting or replacing the biasing members 208.

To impart the biasing force, the biasing members 208 may be configured as, for example, lead screws, ratcheting systems, springs (such as compression springs, torsional springs, gas springs, etc.), or other structural members. Alternatively, the biasing members 208 may include, for example, elastic bands, elastomers, etc., ideally to provide an essentially constant and dynamic biasing force transmitted to the underlying tissue 608 regardless of movement of the tissue securement assemblies towards or away from one another.

FIG. 2 shows a perspective view of a variation having a frame which is adjustable in width and length to accommodate wounds of varying widths. The transverse frame members 200 (at the apexes of the wound) are configured with a hinge point 202 allowing the frame to be adjusted to a varying angle at that point. The system has longitudinal frame members 204 which may be formed of rods or beams which can be oriented to be roughly parallel to the wound length. These longitudinal frame members 204 may be attached to the transverse members at both ends and the entire frame may be supported upon the patient by support members 214 which extend from the frame and into contact against a surface of the skin so that the frame may be maintained at a distance from the patient body. For instance, the support members 214 may be positioned at each corner of the frame and the support members 214 may be adjustably oriented relative to the frame so that the support members 214 may rest upon the skin surface. Furthermore, although the frame is shown to have straightened members, various portions of the frame, such as those members which extend transversely relative to the wound or incision, may be curved or angled to accommodate the anatomy of the patient body. In some embodiments the transverse members are slotted beams where the attachment of the longitudinal members to the transverse members is adjustable such that longitudinal members can be positioned at any point along the transverse members. The transverse members may be composed of two beams with an adjustable and lockable hinge connecting the two beams. This creates an 'A'-frame which allows the frame connecting the two rods to be bent to conform with the abdomen. It is also conceivable that the beams are constructed of one piece but are malleable or have a malleable section such that they can be bent. This section can be made out of a material that is malleable at temperatures above that which would normally be encountered in close proximity to a patient (e.g. higher than 50° C.) but that is rigid at normal room and body temperatures (e.g. less than 40° C.).

The frame may be segmented to allow the frame to adapt to variations of abdominal wall geometry or to allow the biasing members 208 which are coupled to the frame via connectors 206 to apply the force to the corresponding thickness control securement member 212 at a vector which is not parallel to the surface of the abdomen. The segmented frame may contain hinge, telescoping sections, or be malleable such that the frame can be adjusted to an appropriate length, width, and topography to match the abdomen of the patient. The hinge may be made with round holes, elongated slots, or combinations of slots and holes to allow for adjusting the linear length and/or width of the frame as well as the angle at the joint. Such a hinge may utilize a threaded or partially threaded bolt and a nut to allow the hinge to be locked in the desired position. Similarly, linear adjustments may be made with combinations of slots and or holes and one or more pins with reversible locking mechanism such as spring-loaded ball detent or nuts and bolts instead of pins. The lengths of the frame members may be shortened using various methods such as snap-off lengths or cutting the structure if needed or desired. Telescoping tubes or bars may have a friction lock which tightens a collar or collet of the outer tube around the inner tube as a nut is twisted, a cam-lock mechanism, set screws, etc. The angle between segments of the frame running along the length of the abdomen or across the width of the abdomen may be between, e.g., 135 and 180 degrees, while the segments where the cross members at the top and bottom of the frame may form angles, e.g., between 60 and 120 degrees. The overall length and width of the frame are adjustable and may range, e.g., between 5 and 20 inches. With such an adjustable frame, the dimensions can be adjusted as the wound is approximated to bring the frame closer to the closing wound.

With wounds or incisions extending along the abdomen, any number of tissue securement assemblies may be deployed depending on the length of the wound or incision. This may not be equal on both sides of the wound; for example, if an ostomy bag is blocking placement of one or more tissue securement assemblies on one side. The variation shown in FIG. 2 illustrates ten individual tissue securement assemblies applied over the length of the wound or incision; however, the actual number used may vary. The size of the frame may be configurable to account for varying wound sizes. The individual tissue securement assemblies may be spaced varying distances apart from neighboring members along the length of the wound or incision, e.g., 2 to 6 cm. Different amounts of force may be applied at different locations along the edge of the wound or incision, if necessary or desired.

In another embodiment, the frame 500 itself may be comprised at least partially of flexible spring (biasing) members. FIGS. 3A, 3B, 3C, and 3D show a pair of flexible rods 250 joined together at each end via an attachment or coupling member 252 such as a hinge, pivot, or coupling element so that the joined ends are positioned near the apexes of each end of the wound just beyond or near the terminal ends of the wound. The flexible rods 250 may be biased so that their natural unconstrained state is a straightened configuration. When the flexible rods 250 are curved or bent from their straightened configuration, stored energy will bias the rods 300 to revert to their straightened configuration such that the rods 300 will natively impart forces until straight and apply a compressive or tensile load through either direct or indirect connection to the tissue securement assemblies The attachment members 252 of the rods 300 at each end may allow for the rods 300 to pivot or flex relative to one another (e.g., rotational hinge, living hinge, ball joint, etc.) so that the tensioning force may be imparted unhindered. In other alternatives, the first and second rods 300 may be formed of a continuous length of material where the pivoting portions may be reduced in diameter or otherwise configured to allow for the rods 300 to flex and curve accordingly. By changing the material, rod diameter, or other properties of said rods 300, the force applied to the tissue securement assemblies can be varied so that the force is applied uniformly over the length of each rod, and thus the force applied along the edge of the wound. Alternatively, other embodiments may be configured to apply different amounts of force at different locations along the rods 300 so that the approximation force may be applied unevenly. The flexible rods 250 may be made of metal, composites, polymers, or other materials which act as a spring. Alternatively, a torsion spring, compression spring, extension spring, wave spring, or other elastic member can be arranged at the joint between the opposing rods 300 with the joint providing the restoring force to the rods 300.

The first and second rods 300 may be the same or of similar length so that when the rods 300 are curved in opposite directions, the approximation force is uniform along each length. However, in other embodiments, the rods 300 may be of uneven length so that the first rod is relatively shorter than the second rod. Coupling or attachment of uneven rods 300 may result in a naturally curved configurations, but such an embodiment may be used in situations where the wound may not be even or straight. Moreover, multiple rods 300 may be coupled, for example, two rods 300 on a first side and two rods 300 on a second side, so that the approximation force is increased accordingly. Other variations may utilize more than two rods 300 on each side. Yet other embodiments may utilize an uneven number of rods 300, for example, where a single rod is used on one side of the wound while two or more rods 300 may be used on the opposite side of the wound so that the approximation force may be varied along each side of the wound.

In yet further embodiments, the rods 300 themselves may be configured to have various cross-sectional areas. For instance, the rods 300 may be configured to have circular cross-sectional areas or other shapes, such as elliptical, square, rectangular, etc. They may also be configured to have composite cross-sectional areas, such as an I-beam, etc. Depending upon the desired approximation force, rods 300 having the same cross-sectional area may be used with one another while in other variations, rods 300 having different cross-sectional areas may also be used in various combinations with one another depending upon the desired approximating forces and curving characteristics.

In yet another variation, the materials used for fabricating the rods 300 may be varied so that different combinations of materials may be used. For instance, a first rod may be fabricated from a metallic material while the second rod may be fabricated from a plastic or polymeric material while the first and second rods 300 are attached to one another. In other variations, different combinations of rods 300 of different materials may be used with one another. For instance, a combination of a metallic rod and a polymeric rod may be used together on a first side of the wound while a different combination of rod materials may be used on the second side of the wound.

Regardless of the cross-sectional shapes, number of rods 300 used, lengths of the rods 300, materials of the rods 300, etc., the rods 300 may be used in any number of combinations with one another with any of the components or systems described herein.

As described, the biasing compressive or tensile force is applied at a distance removed or remote or at a distance from the surface of the wound or incision and the essentially continuous or non-equilibrating (relatively to intrinsic tissue recoil forces) force, as described herein, is transmitted directly to the underlying tissue 608 via the tissue securement assembly 502. The forces may be transmitted directly to the fixation member 254, to the thickness control securement 256, or to another member attached to the fixation member 254 or thickness control securement 256. The height of the application of the forces above the surface of the wound or incision may be adjusted, limited only in that the biasing rod is positioned above the wound or incision and not in contact with the underlying abdominal contents. The height may be adjusted and secured at various heights depending on the amount of clearance from the underlying tissue 608. As such, the height may be adjusted to have some minimum height clearance above the underlying tissue surface, e.g., 2.0 to 10 mm. Alternatively, the height may be adjusted for each of the devices to be uniform with respect to one another. In any case, the height may remain fully adjustable relative to the underlying tissue surface.

Figure 4A:
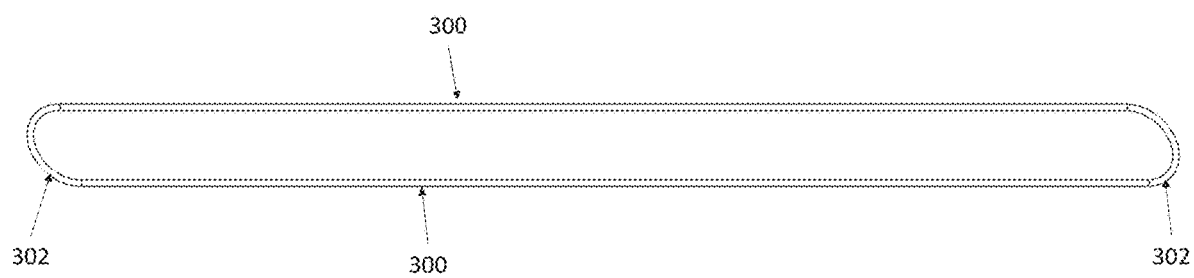
FIG. 4A shows one possible example of a flexible biasing device with a single hinge member at each apex.
Figure 4B:
FIG. 4B shows one possible example of a flexible biasing device with a double hinge member at each apex.
Figure 4C:
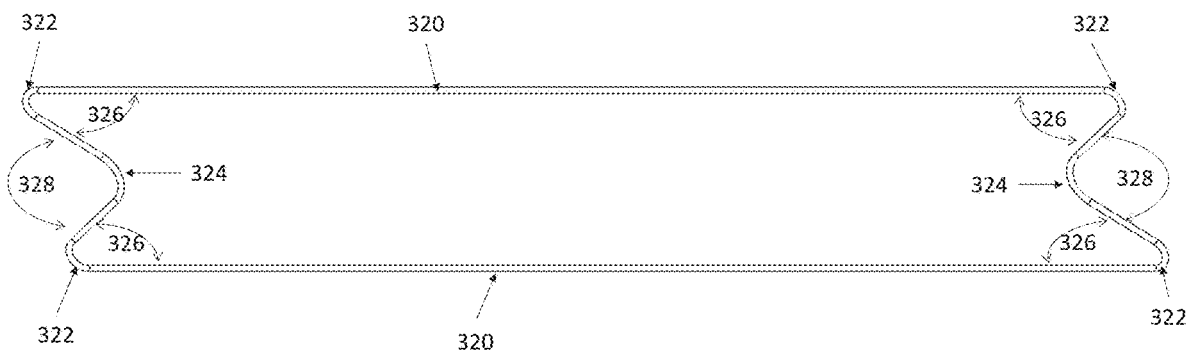
FIG. 4C shows one possible example of a flexible biasing device with a triple hinge member at each apex.

FIGS. 4A, 4B, and 4C show variations of the rods 300 where the end sections are formed of the same material or different material as the rods 300 but where the end section forms differing hinge geometries. This allows for differing force profiles in the rods 300 and different intrinsic levels of approximation of the rods 300. FIG. 4A shows one bend 302 on each end of the rod unit. Depending upon the geometry of the hinge 302 section, the intrinsic relaxed position of this design may allow the lateral rods 300 to be such that there is no separation between the rods 300. In other variations, the lateral rods 300 may be configured to be separated from one another by a predetermined distance such that the lateral rods 300 extend in parallel in their relaxed configuration. The inclusion of a separation distance between the lateral rods 300 may allow for a reduction in force as the edges of the wound are approximated towards one another, if desired.

FIG. 4B shows two bends 312 on each end of the rod unit 310. With this configuration, each of the bends 312 may form an angle 314, e.g., 90 degrees, but in other configurations, the bends 312 may be formed to have an angle of less than 90 degrees or greater than 90 degrees. FIG. 4C shows 3 bends 322 on each end of the rod unit where a first bend 322 on a first rod 320 may form an acute angle 326 of less than 90 degrees and a second bend 324 on a second rod 320 may form a symmetrical acute angle such that a central portion forms a third angle 328 configured in an opposite orientation relative to the first and bends 322, 324. Such designs with two or three or more bends 322, 324 allow for greater separation of the rods 320 in the relaxed position. They also may reduce the forces acting upon the tissue securement assemblies relative to a similar one bend 302 design at the same separation and further allow for the frame 500 to be tuned to a particular range of forces for application to the tissue edges. While these examples are illustrated with a continuous piece of rod material being used to also create the hinge 302, 312, 322, 324 sections, various other hinges or elastic materials could be substituted for the end sections.

In securing the frame 500 relative to the tissue 608, a number of thickness control securement 212 members may be secured to a corresponding fixation member 210 positioned through the tissue 608. The thickness control securement 212 member (as shown in FIG. 6C) may provide a notch, slot, shoulder, or some securement mechanism for holding and retaining the frame 500 when applied for approximating the tissue 608.

Figure 5:
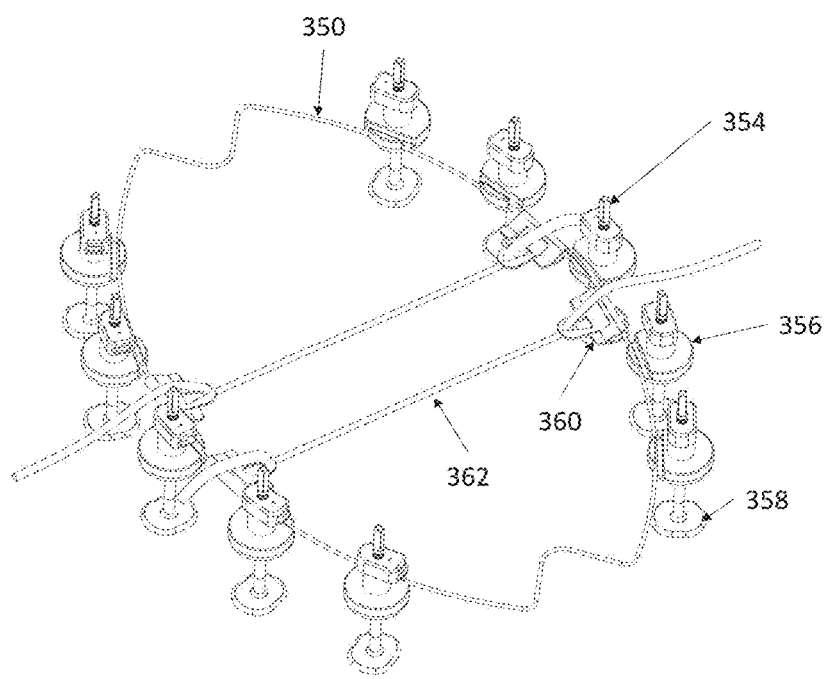
FIG. 5 show elastic elements crossing the wound in addition to the flexible biasing elements around the outside of the wound

The adjustment and attachment of the elastic elements is accomplished through use of systems such as a ladderlock buckle or similar slide adjusters; horn, jam or cam cleats 260; one or more hooks on the length of the elastic element; or by providing a variety of lengths and spring force elements which can be interchanged. FIG. 5 shows an example where the frame 350 has been coupled to each of the thickness control securement elements 356 which are each retained to the tissue via a corresponding fixation member 354 pierced through the tissue thickness and secured via an anchor 358. An elastic element, in this case silicone tubing 362, is connected to the biasing elements on both sides of the wound via jam cleats 360.

Figure 6A:
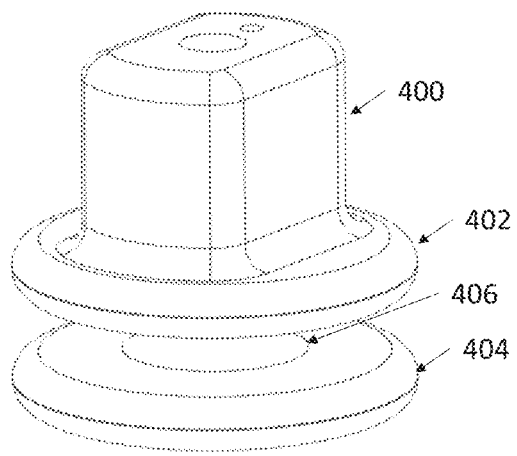
FIGS. 6A and 6B show one example of a possible thickness control securement with a circumferential groove and how a flexible frame rod interacts with it.
Figure 6B:
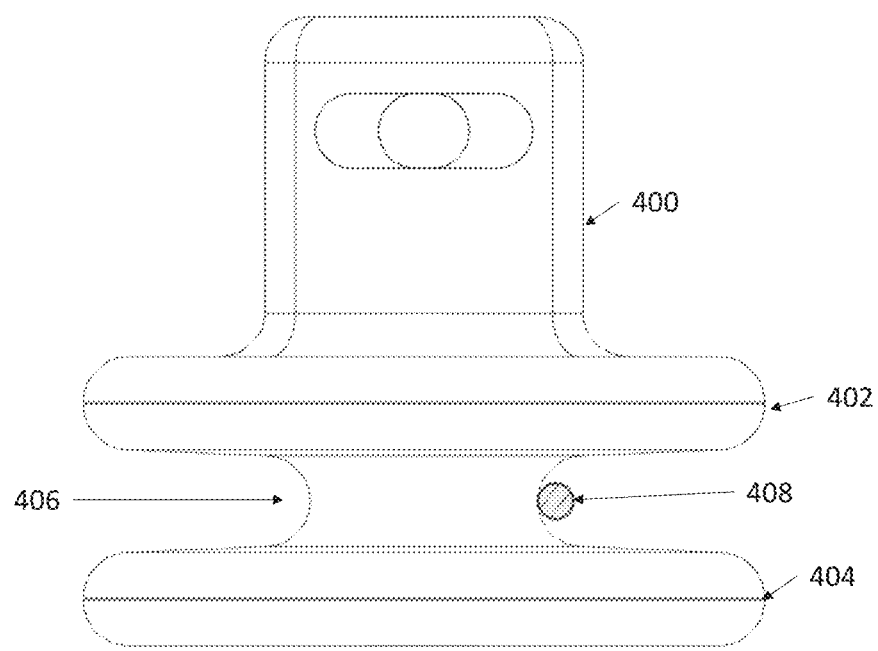

FIG. 6A shows a perspective view of one example of a possible thickness control securement 400 which has a circumferential notch 406. Such a notch 406 may be formed such that its height is the same size or slightly larger than the diameter or thickness of the rod. The thickness control securement 400 member may be slidably adjustable along the fixation member 210 prior to be being secured and the notch may be oriented transversely relative to the height of the thickness control securement 400 member. FIG. 6B shows a side view illustrating how the rod can then be positioned such that it acts on the outside edge of the thickness control securement 400 (relative to the wound which is towards the inside pushing into the circumferential notch). The rims 402, 404 above (away from the skin) and below (towards the skin) maintain the position of the thickness control securement 400 at a distance beyond the skin while limiting that distance so it does not become excessive which would create a large moment tending to cause the fixation member 400 to tilt, thus limiting effective approximation of the wound edges. While the rod 408 is positioned within the notch 406, the biasing force of the rod 408 applied against the notch 406 during use may maintain the positioning of the rod 408 within the notch 406. Furthermore, because of the biasing force, the rod 408 may be free to slide within the notch 406 allowing for the rod 408 to self-adjust its position relative to the thickness control securement 400 member as the tissue approximates over time and shifts its position to prevent any excess torque from being applied to the tissue 608. While this description is of a circumferential notch shown around the entire perimeter of the thickness control securement 400, such a notch 406 may also be formed around only part of the perimeter.

Figure 6C:
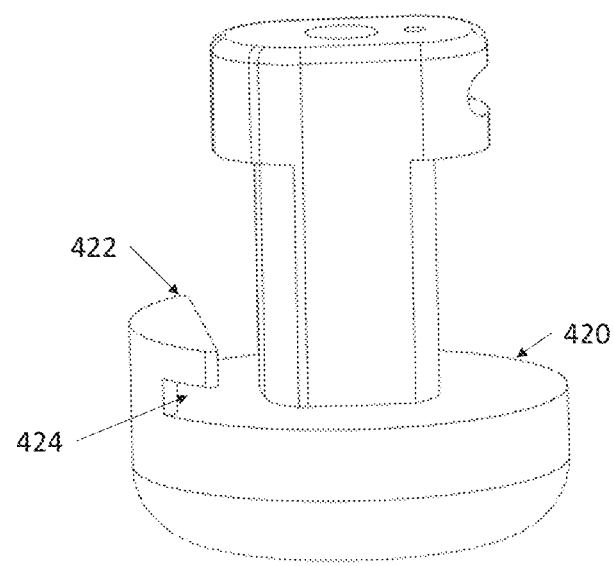
FIGS. 6C and 6D show one example of a possible thickness control securement with an undercut and how a flexible frame rod interacts with it.
Figure 6D:
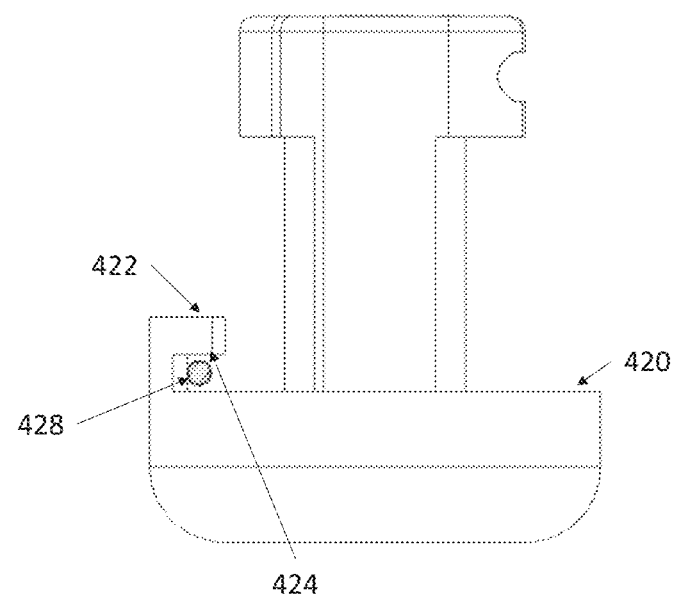

Alternatively, FIG. 6C shows a perspective view of a possible thickness control securement 400 which has a slot 420 with an undercut 424. A similar geometry can be made using one or more protruding tabs with undercuts 424. Such a slot may possess sufficient width to allow the rod to pass into the undercut 424 or alternatively sufficient space between the protruding tabs and the adjacent radial surface of the thickness control securement 400 to allow the rod into the undercut 424. The undercut 424 is so sized that in one or more locations it engages with the rod, limiting the ability of the rod to move away from the skin. In the case of a round rod, the undercut 424 is formed such that the vertical free height is equal to or greater than the diameter of the round rod and the horizontal overhang 422 is equal to or greater than the radius of the rod. There are other dimensional combinations which allow the rod to engage with the undercut 424 but may be less robust at resisting the rod from disengaging with the skin support. The surface of the thickness control securement 400 between the rod and the surface of the skin prevents the rod from moving inward towards the abdominal cavity. FIG. 6D shows a side view of one engagement method between the biasing rod and thickness control securement 400, with the biasing rod shown pulling on the protruding tab.

Figure 6E:
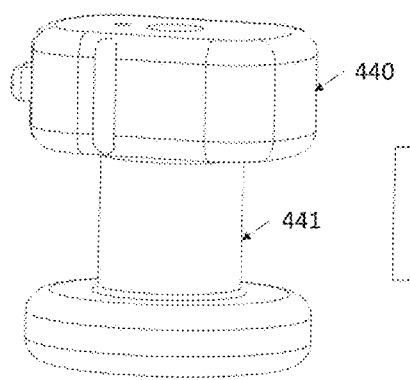
FIGS. 6E to 6F show one example of a possible thickness control securement with a spring clip and connection to a flexible frame rod.
Figures 1, 6E:
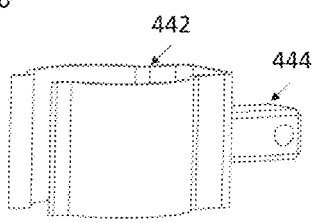
Figures 2, 6E:
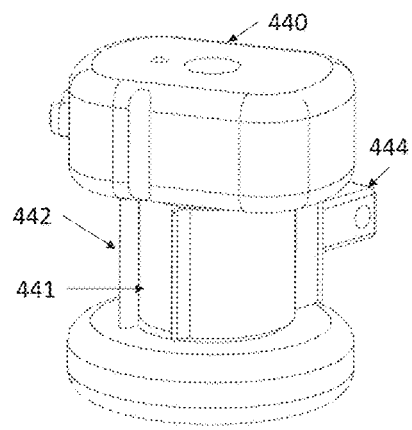
Figure 6F:
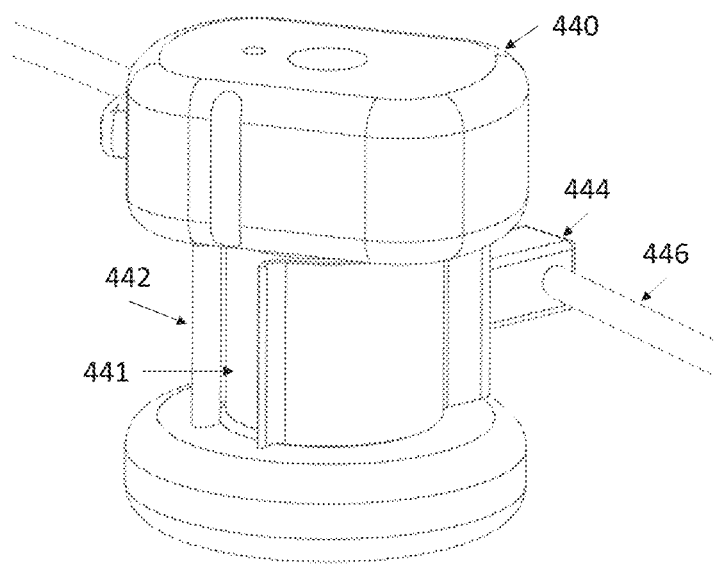

FIGS. 6E and 6F show perspective views of yet another possible thickness control securement 400 which utilizes a separate semi-cylindrical clip to connect the rods 428 to the thickness control securement 400. A similar structure can be utilized between the rods 300 and the fixation member 400 rather than the thickness control securement 400. FIG. 6E shows the thickness control securement 440 member defining a tubular receiving portion 441 for engaging with a separate clip shown in FIG. 6E-1 which has a connector 444 through which the rod may be slidably positioned. The clip 442, shown in the example as a spring clip 442, may be secured over the tubular receiving portion 441 to provide a securement between the components such that the connector 444 may extend away from the clip 442 as a singular unit, as shown in the perspective view of FIG. 6E-2.

FIG. 6F shows a perspective view of the assembled components with the rod 446 slidably positioned through the connector 444 while the clip 442 is secured over the tubular receiving portion 441.

In some cases, it may be desirable to increase the approximating forces applied by the flexible rods. If a higher force is required over the entire length of the wound, stiffer biasing rods may be utilized. However, if locally higher forces are desired, an elastic element can be added at one or more positions along the longitudinal length of the wound. These elastic elements may be connected directly or indirectly to either the biasing rods or to the tissue securement assemblies. The elastic elements may consist of elastic tubing 362 or strips, springs, or other mechanisms which exert a contractive force tending to add additional approximating forces to the biasing elements. It is desirable that the supplemental elastic elements are attached to the biasing rods or the tissue securement assemblies at a level above the surface of the skin so that the elastic element crosses the wound above any tissues, reducing the risks of the elastic elements damaging tissues. Additionally, it is ideal if the elastic elements able to be easily removed or adjusted both to enable adjusting the forces applied to the wound as well as to enable the temporary removal of the elastic elements crossing above the wound to improve access for wound care. Attachment of supplemental elements only to the biasing mechanism allows for easy removal in the event of required access to the abdominal cavity.

Figure 7A:
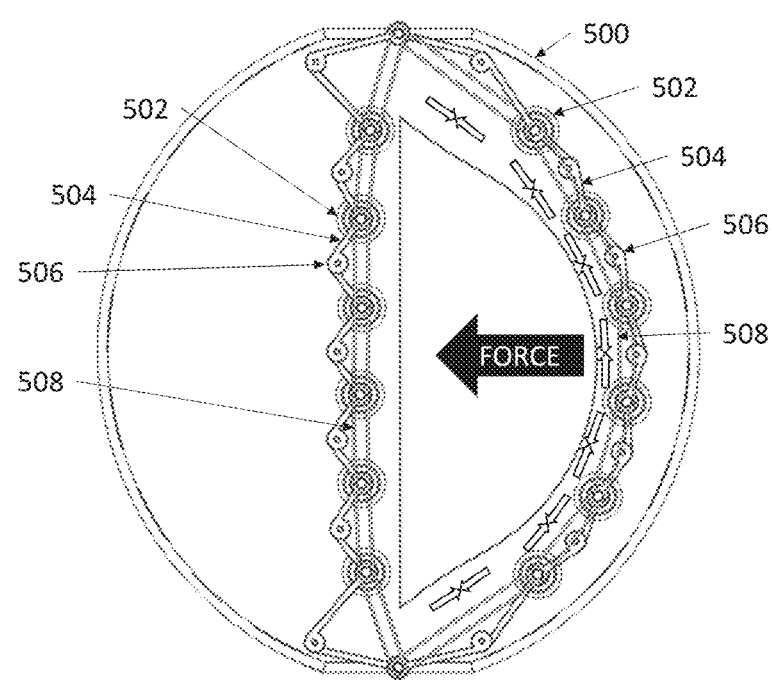
FIGS. 7A to 7C show various views of an embodiment of a tissue approximation system which may utilize biasing members and linkages between adjacent tissue securement assemblies where the biasing members acting against the series of tissue securement assemblies tend to approximate the edges of the wound.
Figure 7B:
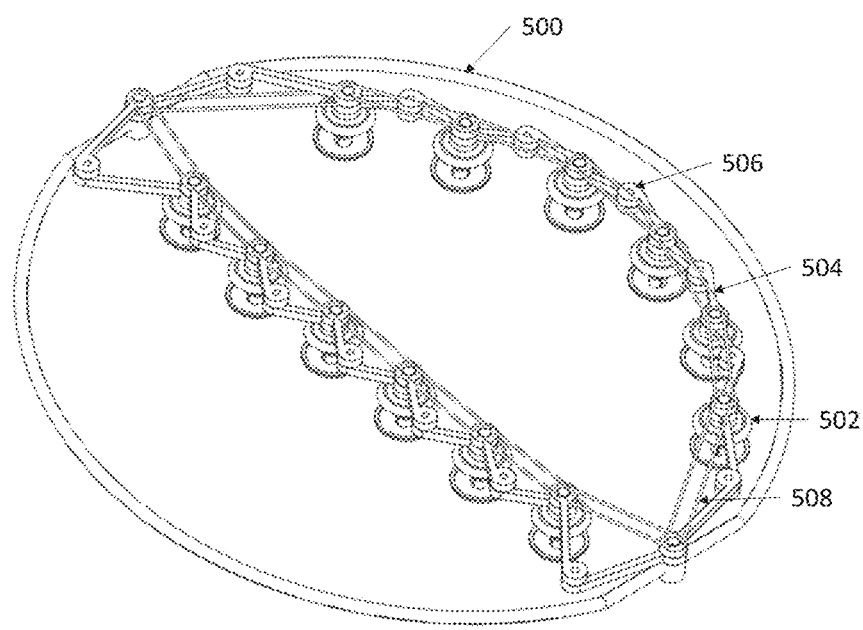
Figure 7C:
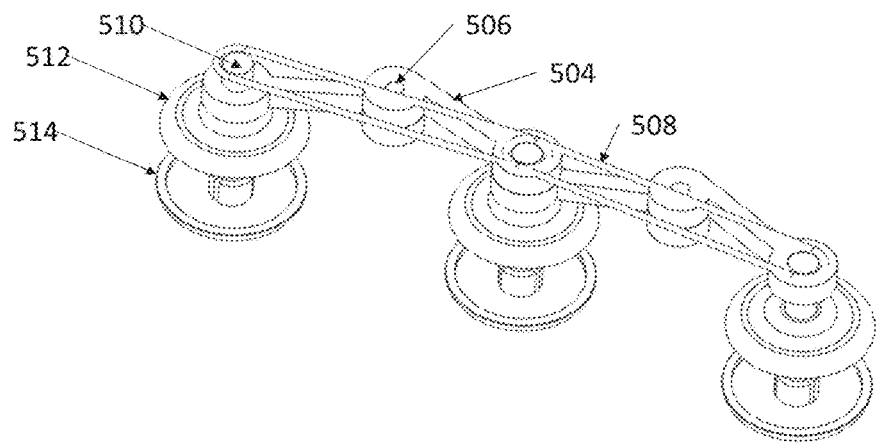

An alternative embodiment, shown in the top assembly, perspective, and detail perspective views of FIGS. 7A, 7B, and 7C, uses two or more linkages 504 between adjacent tissue securement points to allow for limited degrees of freedom of motion. Each set of adjacent tissue securement assemblies 502 are placed under tension towards each other via a biasing member 508 such as a spring or elastic member, as shown by the arrows directed to one another indicating the tensioning force. This biasing member 508 can run directly from one tissue securement point to the adjacent tissue securement point using a spring, elastic band, or other force agent. The force can also be created through the linkage 504 hinge points using torsion springs, compression springs between acute angled linkage 504 members, or tension via springs or bands from outer most linkage 504 hinge points to adjacent outer most linkage 504 hinge points. This system allows for each tissue securement assembly 502 to move somewhat independently of the others to normalize tension along the entire system.

The chain of connected linkages 504 and tissue securement assemblies 512 are anchored to a rigid frame 500 at or near each apex of the incision. These fixed anchor points cause the forces pulling the tissue securement assemblies 512 on one side of the incision to create a resultant force, as shown in the FIG. 7A, toward the wound at each tissue anchor point. Distances from each tissue anchor point to adjacent points along the chain reduce in length causing the force required to pull tissues toward the incision margin. The system allows forces pulling along the length of the wound at each tissue securement point to balance out with forces pulling from the tissue incision apex to the opposing apex, yielding a force which tends to close the wound or incision. In a more simplified version, there is no mechanical linkage 504 or hinged segments between adjacent tissue securement assemblies but rather only spring members which tend to pull neighboring tissue securement assemblies toward each other on the same side of the wound, shortening the chord length of the curve described by the various tissue securement assemblies, tending said curve to linear form. With both apexes anchored and similar chains of tissue securement assemblies on both sides of the wound, as the curve become linear, the wound tends to close.

FIG. 7A shows an anterior view of the assembly over a wound with one side near full extension and the opposing side close to the midline. This representation uses elastic bands as the spring members 508 between each tissue securement assembly 502 and end anchor points. The elastic bands may be made of thermoplastic elastomer, silicone rubber, or other elastomeric substance. They may be bands which are slipped over the shaft of the fixation members 510 or otherwise hooked onto features of the thickness control securement 512 or hinge 506. The spring members' elastic modulus and length are selected such that the resultant force on the anchors 258 tends to move tissue 608 to the midline is in a range which causes tissue approximation without undue discomfort or tissue damage (e.g. 100 g to 400 g). FIG. 7B shows an isometric view of the frame 500, linkages 504 and tissue securement assemblies. FIG. 7C shows a section of linkages 504 coupled via hinges 506 between tissue securement assemblies and the spring members 508 that bridge from each tissue securement assemblies to adjacent assemblies.

In some cases, it may be desirable to increase the approximating forces applied by the spring members. If a higher force is required over the entire length of the wound, stiffer spring members may be utilized. However, if locally higher forces are desired, an elastic element can be added at one or more positions along the longitudinal length of the wound. These elastic elements may be connected directly or indirectly to either the linkage 504 elements or to the tissue securement assemblies. The elastic elements may comprise elastic tubing 362 or strips, springs, or other mechanisms which exert a contractive force which tends to add additional approximating forces to the system of linkages. It is desirable that the supplemental elastic elements are attached to the linkage 504 elements or the tissue securement assemblies at a level above the surface of the skin so that the elastic element crosses the wound above any tissues, reducing the risks of the elastic elements damaging tissues. Additionally, it is ideal if the elastic elements able to be easily removed or adjusted both to enable adjusting the forces applied to the wound as well as to enable the temporary removal of the elastic elements crossing above the wound to improve access for wound care.

The adjustment and attachment of the elastic elements is accomplished through use of systems such as a ladderlock buckle or similar slide adjusters; horn, jam or cam cleats 360; one or more hooks on the length of the elastic element; or by providing a variety of lengths and spring force elements which can be interchanged.

Figure 8A:
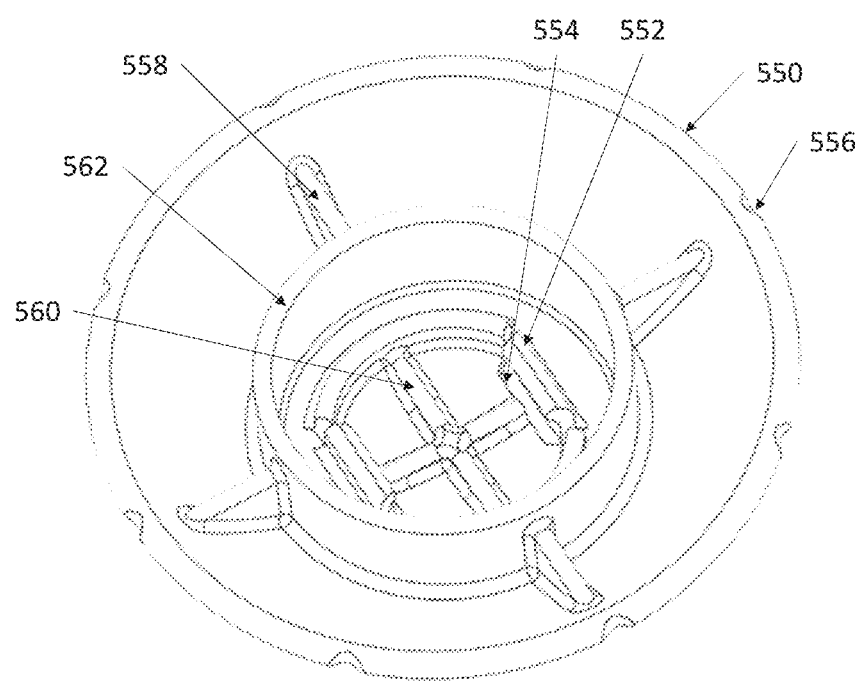
FIGS. 8A and 8B show one possible example of an anchor cup used to protect the viscera during device implantation. The anchor cup may have provisions to releasably hold the anchor and provide support to the anchor member, allowing the fixation member to be screwed to or otherwise attached to the anchor member.
Figure 8B:
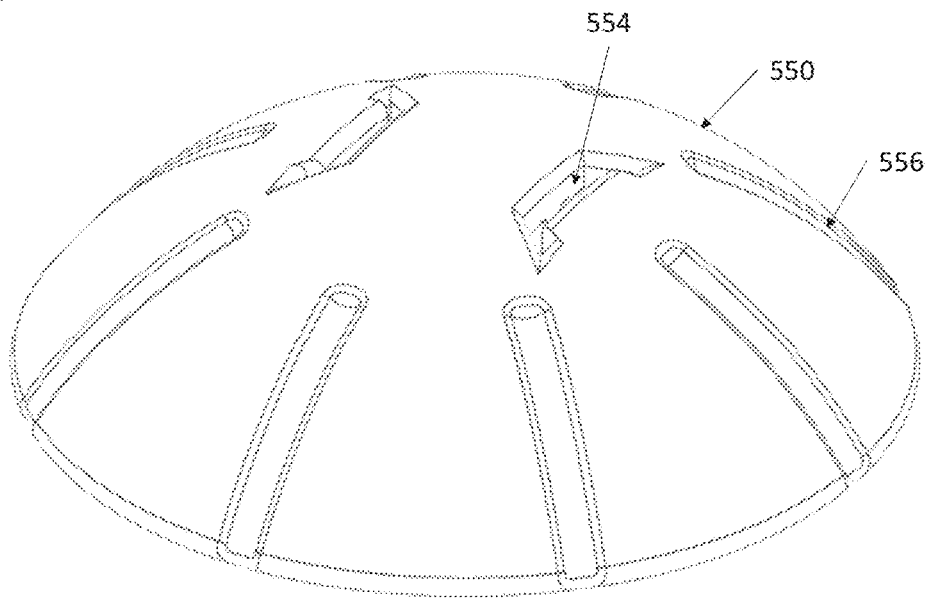

For installation of the fixation members 510 and anchors 514, including the attachment of the fixation member 510 to the anchor 514, additional instruments may be provided to facilitate the procedure as well as to protect the medical staff and patient from injury. Especially in the case of a sharp fixation member 510 being pushed from the exterior of the abdomen towards the interior, it is desirable to avoid puncturing the organs of the patient or the hand of the surgical staff. An anchor cup 550 as shown in the bottom and top perspective views in FIGS. 8A and 8B is one possible example of protection for viscera and surgeon's hand during device implantation. The anchor cup 550 may have provisions to releasably hold the anchor 514 and provide support to the anchor member, allowing the fixation member 510 to be threaded or otherwise attached to the anchor member. Such a cup 550 may be made of plastic, stainless steel, titanium, aluminum, other materials which are suitable for use in contact with tissue 608 for short periods of time, or combinations of such materials.

In the embodiment shown, the cup 550 is semi-spherical or otherwise curved in shape to fit in the palm and fingers of the hand. However, any shape (oval, square, rectangular, parabolic, polygonal, etc.) may be used which provides a method to grip the cup 550 and anchor 514 while simultaneously protecting the surgeon from inadvertent contact with the sharp point of the fixation member 210. During use, the surgeon may hold the anchor cup 550 in a first hand such that the anchor cup 550 is positioned on the interior of the body in proximity to where the fixation member 210 is to be penetrated though the tissue thickness. The surgeon may then advance the fixation member 210 with their second hand such that the penetrating tip may pass through the tissue thickness and directly into the concave portion of the anchor cup 550 held in the surgeon's first hand so that the surgeon may then couple the anchor 514 positioned within the anchor cup 550 with the fixation member 210 for securement, as described in further detail below.

FIG. 8A shows snap 552 features on the concave surface of the cup 550 which are used to releasably engage with the anchor 514 and receiving features 562 restrict it from rotating while the fixation member 210 is threaded onto the anchor 514. On both the convex and concave sides of the cup 550, visible slits 554 exist to create the necessary length of cantilever beam for the snap 552 features enabling the snaps 552 to releasably engage with the anchor 514 for many cycles without excessive force and without exceeding the mechanical limits of the material from which the cup 550 is made. Other features on the cup 550 may be provided to increase stiffness (e.g. ribs 558, 560), provide visibility (e.g. openings or transparent sections), improve guidance (e.g. conical or tapered guide surfaces), or features 556 to enhance the ability of the surgeon to grasp the cup 550 and prevent undesired rotation (e.g. textures, scallops, finger rings, etc.)

Figure 9A:
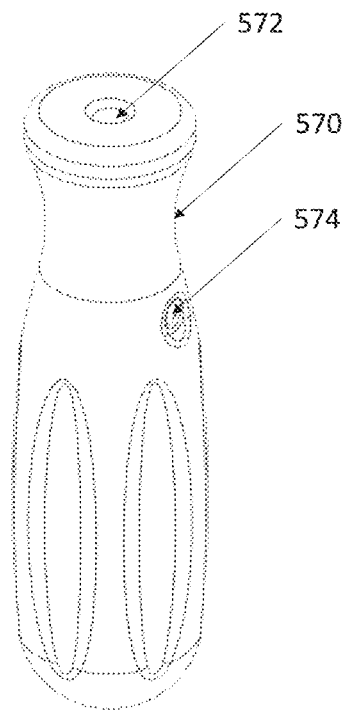
FIG. 9A shows one possible example of a handle used to drive the fixation member through the tissue and screw or otherwise attach it to the anchor member which may be held in the anchor cup.
Figure 9B:
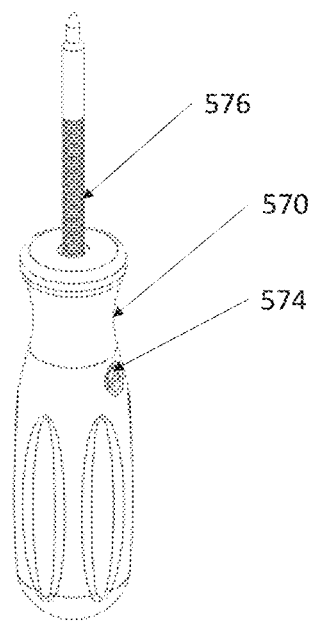
FIG. 9B shows the fixation member inserted into the handle.

A handle 570 as shown in perspective views of FIGS. 9A and 9B in one possible example of a device which may be used to drive the fixation member 210 through the tissue 608 and screw or otherwise attach it to the anchor member which may be held in the anchor cup 550. The handle 570 may have a ball detent 574 or snap 552 which is positioned within a receiving channel 572 and which engages with a mating feature on the fixation member 576 when inserted within the receiving channel 572 in a releasable fashion. The handle 570 also may have a square, hexagonal, or other polygonal shaped male or female feature which mates with a similar feature on the fixation member 576 to provide the ability to rotate the fixation member 576 to screw it to the anchor 514. In the example shown, a spring-loaded ball plunger is located in the handle 570 such that the ball is protruding beyond the square profile which mates with the square profile on the end of the fixation member 576. The ball of the plunger thereby provides friction against the square end of the fixation member 576 when it is inserted into the handle 570. In some embodiments, an undercut 424 or depression is made on the square portion of the fixation member 576 into which the ball plunger more positively mates, create a higher retention force of the fixation member 576 in the handle 570. While this description discusses a square pocket in the handle 570 mating with a square profile on the fixation member, the male/female portions of this arrangement may be reversed. In addition, any shape may be used which provides the ability of the handle 570 to provide a rotational moment around the axis of the fixation member 576 such that the fixation member 576 can be threaded to the anchor 514. In this embodiment, detachment of the fixation member 576 from the handle 570 is achieved by pulling the handle 570 axially off the fixation member 576 with sufficient force to overcome the resistance provided by the ball plunger.

Figure 10A:
FIGS. 10A and 10B show the anchor cup and handle being used together for installation of the fixation member and attachment of the anchor to the fixation member.
Figure 10B:

FIGS. 10A and 10B perspective views showing the cup 602 and handle 600 being utilized together for installation of the fixation member 576 and anchor 514. A geared handle 600, such as a manual drill, is also possible to reduce surgeon efforts at rotational insertion. Such a manual geared drill is described in U.S. Pat. No. 3,823,755, which is incorporated by reference in its entirety for any purpose herein. By utilizing such a manual drill, for example, such that the output shaft of the drill is removably coupled to the fixation member 576 and with the gearing of the manual drill arranged such that the output shaft rotates, e.g., between 2 and 5 times, for each rotation of the input handle 600, the surgeon would then need to rotate the hand fewer times to fully engage the threads of the fixation member 576 with the threads of the anchor member, both speeding up the procedure as well as reducing the possible fatigue the surgeon may experience due to having to perform multiple rotations of each fixation member 576 across multiple fixation members 576 in the abdominal wall.

To utilize the cup 602 and handle 600 described above to install the fixation member 576 and anchor member: 1) the anchor member is reversibly attached to the inside of the cup 602; 2) the fixation member 576 is reversibly attached to the handle 600; 3) the surgeon holds the cup 602 in one hand on the interior side of the abdominal wall in the approximate location where the fixation member 576 will be installed; 4) the surgeon inserts the fixation member 576 through the tissues 608 from the outside of the abdomen towards the inside of the abdomen in the desired location. Pressure is applied to the handle 600 along the axis of the fixation member 576 to drive the fixation member 576 through the tissues 608; 5) the surgeon is no longer able to drive the fixation member 576 further into the abdomen when the tip of the fixation member 576 contacts the cup 602 or the anchor 514 attached to the cup 602; 6) the surgeon can partially remove (e.g. tilt) the cup 602 from the inside wall of the abdomen to visualize the location of the tip of the fixation member 576 to the connecting element of the anchor member; 7) the surgeon adjusts the position of the cup 602 and anchor member such that the tip 604 of the fixation member 576 is in contact with the connecting element 606 of the anchor member; 8) the surgeon rotates the handle 600 and thereby the fixation member 576 while holding the cup 602 stationary, thereby engaging the connecting elements 606 of the anchor 514 and fixation members 576; 9) the surgeon pulls the handle 600 away from the abdomen along the axis of the fixation member 576, disengaging the handle 600 from the fixation member 576; 10) the surgeon holds the fixation member 576 with their hand and pulls the cup 602 away from the anchor member disengaging the cup 602 from the anchor member; and 11) the surgeon installs additional anchor 514 and fixation members 576 in a similar fashion and installs the thickness control securement 212 and the biasing mechanisms described above. The surgeon may make skin incisions with a scalpel or other tool prior to step #4 to facilitate tissue penetration.

As described herein, the fixation member 576 generally comprises a slender elongate element. In some cases, the fixation member 576 is solid, in others it may be hollow or otherwise define one or more lumens. The fixation member 576 may have a sharp, atraumatic, or acute tip on one or both ends with such tip being useful for penetrating the fixation member 576 through tissue 608. The sharp tip may be removably attached to the fixation member 576, removable by cutting or breaking off, or be covered by other elements of the invention to prevent inadvertent injury to the patient or others. The exterior surface of the fixation member 576 may be smooth or may have various features to enable a positive engagement with the thickness control securement 576. These engagement features may take the form of threads, ridges, rings, knurling, ratchet fingers, etc. In order to facilitate adapting to varying tissue thicknesses, it is desirable to be able to shorten a longer fixation member 576. This shortening may be accomplished through cutting, disengaging, or breaking of the fixation member 576. For either cutting or breaking it is foreseeable to provide thinner or weaker points to make the cutting or breaking process easier or to define appropriate locations at which to shorten the fixation member 576. For engagement with the anchor 514, it is desirable in some embodiments to include features on the fixation member 576 which engage with features of the anchor 514 to connect the anchor 514 to the fixation member 576 either permanently or detachably. These include threads, quarter-turn connectors, snap fits, ball detents 574, etc. The fixation member 576 may be made from a any of a variety of materials including thermoplastics, thermosets, composites, ceramics, or metals.

The shaft of the fixation member 576 may be of a constant shape, for example round of constant diameter. In other cases it may be desirable to have a square, rectangular, or other polygonal shaft for the fixation member 576. It is also foreseeable that a transition between various shapes/dimensions is desirable. One example of this would be a triangular tapered cross section forming the penetrating tip of the fixation member 576 with the triangular section changing into a round section for a majority of the shaft length, and the opposite end of the fixation member 576 having a polygonal section to engage with a handle 570 or driver as described elsewhere in this document. In some cases it may be desirable to have a change in dimensions of a shaft (e.g., a tapered, pointed, round section for penetrating tissue 608; a section of a relatively small diameter (e.g., 2-3 mm) with threads for engagement with the anchor 514; a primary shaft diameter of a larger diameter (e.g., 4-6 mm), and a section with ribs of stepped diameters). One concern with a fixation member 576 with forces applied to it is possible damage/ripping of the tissue 608 that the fixation member 576 is penetrating. To mitigate this tissue damage the shaft can be constructed and place in the tissue 608 to present a broader or more obtuse surface towards the tissue 608 under compression. Some examples of possible shapes are triangles, tear-drops, and concave (semi-lunar) cross-sections.

The anchor 514 may be integral with, permanently attachable to, or removably attachable to the fixation member 576. In the case of permanent attachment, the opposing end of the fixation member 576 would need to be utilized to penetrate the tissues 608 of the abdominal wall (from the inside toward the outside). The anchor 258 may be composed of any of a variety of materials including thermoplastics, thermosets, composites, ceramics, or metals. For engagement with the fixation member 576, it is desirable in some embodiments to include features on the fixation member 576 which engage with features of the anchor 514 to connect the anchor 514 to the fixation member 576 either permanently or detachably. These include threads, quarter-turn connectors, snap fits, ball detents 574 that create a universal joint, etc. In general, the anchor 514 has lateral extents which exceed the diameter of the fixation member 576 so as to resist the tendency of the tissue securement assembly 502 to pull out of the abdomen. The anchor member being configured such that it generally has no exposed sharp edges which may tend to injure or cut tissue of the abdominal wall or especially the viscera contained within the abdomen.

Another variation of the apparatus utilizes an inflatable or collapsible retention member in lieu of a rigid anchor 514 to maintain position of the fixation member 576 relative to the tissue 608, as described in further detail below. An inflation member, having an inflatable balloon, or otherwise expandable member located on its end may be advanced through the lumen of the fixation member 576 for securing the apparatus to the tissue 608. In this variation, the inflation member may have an elongate shaft with a valve member positioned at the other end of the device. The fixation member 576 may be initially introduced through the tissue 608 using, e.g., a trocar having a sharpened introducer tip which may be removed after insertion. Alternatively, the fixation member 576, may be introduced directly into the tissue 608 via a variation of the fixation member 576 having a sharpened tip which may be removed after insertion such as an obturator being removed from a trocar, or it may be covered with a threaded cap that serves as the internal fixation member 576.

In either case, the fixation member 576 may define a hollow lumen through which the inflation member may be advanced after placement of the fixation member 576. With the end of the inflation member inserted into the abdominal cavity, the inflatable balloon may be expanded via the introduction of a liquid or gas through the elongate shaft. After inflation, the valve member may be closed or otherwise sealed to maintain the expanded configuration of the balloon against the interior surface of the tissue 608. The inflation member may be secured to the fixation member 576 to maintain traction of the device relative to the tissue 608.

By utilizing a medical balloon by itself or together with a stiffening system (similar to a cardiac stent), it is possible to remove the fixation member 576 from the abdominal wall without reopening the abdomen. This can be achieved by deflating the balloon and pulling the inflation member and pin out through the skin. If a fixation member 576 is utilized with a rigid, non-collapsing head, it can be removed at a final closure procedure.

Use of a medical balloon also enables an alternate treatment involving interventional radiology whereby utilizing imaging (such as ultrasound or other imaging technologies), the surgeon or interventional radiologist can visualize the location of an inserter (e.g., trocar) in the tissue 608 and slowly insert it until it penetrates the interior layers of the abdominal wall without penetrating the viscera. After the trocar has penetrated to the appropriate depth, it can be withdrawn and the inflation member and fixation member 576 can be advanced through the hole created. Once the balloon is at the appropriate depth, the balloon can be inflated retaining the fixation member 576 in the abdomen.

While the example illustrates medical balloons implemented as anchors 514, any number of reconfigurable anchoring mechanisms may be used aside from inflatable or expandable balloons. For example, other variations for anchors 514 may utilize an expandable mesh or cage, while additional variations may utilize an elongate member which is reconfigurable, for instance, by pivoting or moving from a low-profile configuration for delivery to a transverse or angled configuration, which prevents the anchor 514 from being pulled proximally for securement against the tissue 608. Yet other variations may utilize reconfigurable anchoring mechanisms which incorporate barbed features or other tissue securement features. In any of the device variations described herein, any number of anchoring variations may be utilized in any number of combinations as so desired.

The thickness control securement 512 may be attached to or held in position on the fixation member 576 in a variety of ways. As described above, the thickness control securement 512 may define a lumen which allows it to be axially assembled to the fixation member 576. To retain the thickness control securement 512 in position on the fixation member 576 so that the fixation member 576 and anchor 514 are restricted in ability to move further into the abdomen, it may utilize a spring detent retention mechanism (with or without a manual button), threads, ratchets, or other locking mechanisms. In addition, rather than assembling axially it may be configured to clip onto the fixation member 576 from the side. This may include being configured with a longitudinal opening on a side of the thickness control securement 512 and spring features to grasp the fixation member 576 or two or more semi-cylindrical sections which clamp around the fixation member 576.

Each of the thickness control securements 512 may incorporate an interface member 260 made from a soft and atraumatic material (e.g., foam 654, pads, silicone, fluid-filled balloon, etc.) to cushion the thickness control securements 512 against the surface of the skin and to possibly elute antiseptics to reduce risk of pin track infection. Alternatively, the interface member 260 may be a separate part positioned between the thickness control securements 512 and the underlying tissue 608 to present an atraumatic interface as well as to distribute any forces over the interface member 260, against the tissue 608. In addition, to accommodate patient movement during dynamic events (e.g., bending over, coughing, etc.), features such as an interface member 260 may prevent direct impingement or rubbing of the device against the skin. The interface member 260 may be pre-loaded to a compressive force that is below a threshold level which would otherwise cause local ischemia or injury to the tissue 608.

This interface member 260 may also have antimicrobial compounds on the surface or within to prevent infection at the pin site (e.g., Biopatch®, Johnson & Johnson Corp., NJ). Additionally and/or optionally, the interface member 260 may be configured as transparent or translucent padding having an irradiating light incorporated to illuminate the skin surrounding the skin fenestration area with, e.g., UV light, for reduction or elimination of harmful bacteria in this region. A battery could power a UV LED source for clinical effect for several days or weeks.

In one variation, a device such as a tonometer or intra-compartmental pressure monitor could be used to measure pressure applied to the tissue 608 and aid in preventing excessive compression and tissue damage. Pressures on tissue of less than 32 mm Hg typically do not cause necrosis and as such, pressure levels at or below that reading would allow for ideal deployment. The tonometer may thus help to set a sub-injurious level of compression of the tissue sandwiched between the thickness control securements 512, and backstop or shoulder.

Figure 11A:
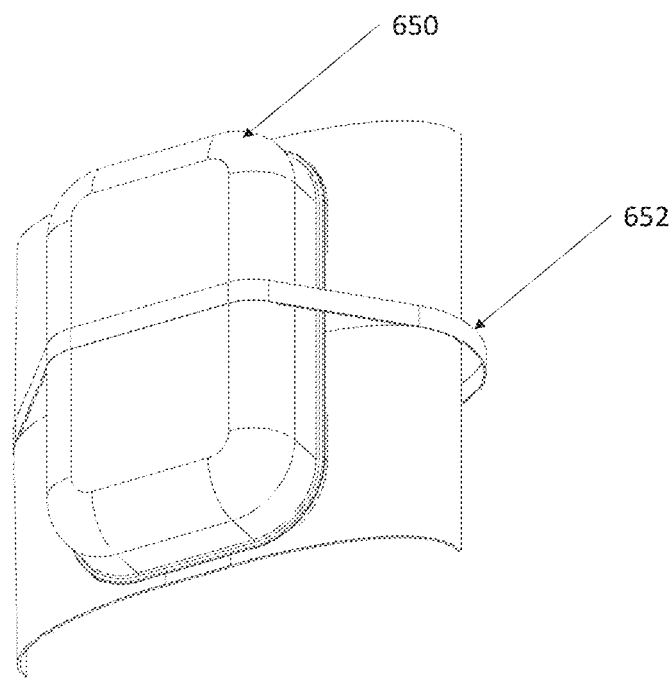
FIGS. 11A and 11B show a protective cover which may be used to limit potential accidental damage to tissue caused by external physical forces acting on the tissue securement assemblies or frame.
Figure 11B:
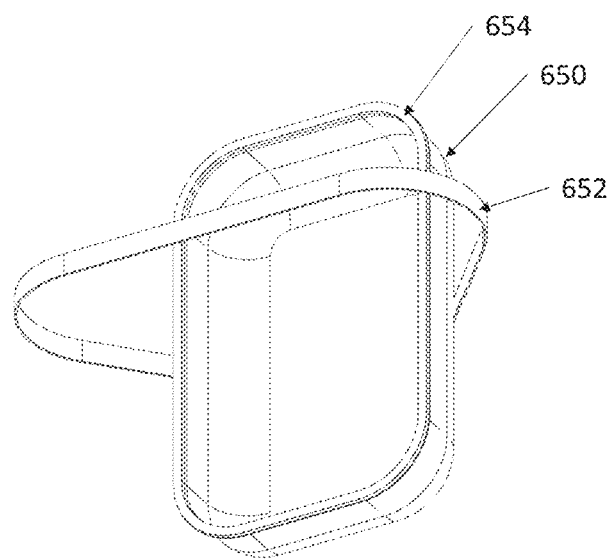

Additionally and/or optionally, a protective covering or shell 650 as shown in FIGS. 11A and 11B may be applied around the entire external apparatus to prevent any inadvertent forces from acting upon the individual elements or regions of the device. This would prevent or inhibit the patient or others from intentionally or inadvertently pressing against the device after implantation which could cause the apparatus to exert pressure internally within the abdominal cavity and potentially cause damage to portions of the bowel or other organs in proximity to the tissue securement assemblies. If the covering or shell 650 completely encloses the apparatus, then the outer perimeter of the turtle shell may contact the torso first if there is an external load put on the shell 650, thus preventing contact against the apparatus. The edges of the covering or shell 650 may contact and press the tissue 608 (most likely skin) well outboard of the wound zone and the external apparatus, resulting in no fixation member 510 displacement and only minor patient discomfort of the covering or shell 650 contact with uninvolved tissue 608. In some embodiments it may be desirable to add a foam or other soft gasketing material to the edge 654 of the cover 650 where it contacts the tissues to cushion and protect the tissue 608 from the rigid or semi-rigid cover. The cover may be strapped around the body using fabric or elastic straps 652 or may be secured to the tissue 608 through the use of removable temporary adhesives which are known to be compatible with sticking to skin.

Additional features may be included to prevent unintentional or malicious tampering with the systems described above. Such optional safety features may include atraumatic pin tips, snag protection features, uncommon fastener heads, locks, tamper resistant connections, etc.

In this or any of the variations described here, the thickness control securements 512 may be separate components from the anchors 514 and fixation members 210. However, other variations may incorporate each of the components as being attached or integrated with one another.

The applications of the devices and methods discussed above are not limited to wound closure but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A tissue securement assembly, comprising:
   a fixation member having a length;
   a thickness control securement member defining a receiving channel through which the fixation member is adjustably securable along the length, wherein the thickness control securement member further defines a receiving notch formed at least partially around a perimeter of the thickness control securement member such that the notch is oriented transversely relative to a height of the thickness control securement member; and
   a frame which is adjustably securable to the thickness control securement member when a portion of the frame is positioned within the notch such that the frame is oriented transversely relative to the height of the thickness control securement member,
   wherein the frame has a relaxed configuration and a biasing configuration which imparts a biasing force generated by the frame against the notch of the thickness control securement member when in the biasing configuration such that the biasing force is applied at a distance from tissue to be approximated via the fixation member.

2. The assembly of claim 1 further comprising a second fixation member having a second length and a second thickness control securement member which is adjustably securable along the second length such that the frame is adjustably securable between the thickness control securement member and the second thickness control securement member.

3. The assembly of claim 2 wherein the frame is comprised of a first elongate member securable to the thickness control securement member and a second elongate member securable to the second thickness control securement member and coupled to the first elongate member.

4. The assembly of claim 1 further comprising an anchor positionable near or at a proximal end of the length of the fixation member.

5. The assembly of claim 1 further comprising one or more biasing members operably coupled to the thickness control securement member.

6. The assembly of claim 1 wherein the frame comprises an elongate length and width which is sized to be positioned in parallel externally of a wound or incision.

7. The assembly of claim 1 wherein the frame is comprised of one or more segmented rod members.

8. The assembly of claim 1 wherein the frame is comprised a continuous material.

9. The assembly of claim 1 wherein the frame defines one or more bends.

10. The assembly of claim 1 wherein the fixation member is slidably adjustable through the receiving channel.

11. The assembly of claim 1 wherein the portion of the frame is slidably positioned within the receiving notch.

12. The assembly of claim 1 further comprising an anchor cup sized to be positioned within a body lumen and defining a portion for receiving a tip of the fixation member.

13. The assembly of claim 1 further comprising a handle removably securable to the fixation member.

14. The assembly of claim 1 further comprising a protective covering or shell positionable over the tissue securement assembly.

15. A tissue securement assembly, comprising:
    a first fixation member having a first length;
    a first thickness control securement member defining a first receiving channel through which the first fixation member is adjustably securable along the first length, wherein the first thickness control securement member further defines a first receiving notch formed at least partially around a first perimeter of the first thickness control securement member such that the first notch is oriented transversely relative to a first height of the first thickness control securement member; and
    a second fixation member having a second length;
    a second thickness control securement member defining a second receiving channel through which the second fixation member is adjustably securable along the second length, wherein the second thickness control securement member further defines a second receiving notch formed at least partially around a second perimeter of the second thickness control securement member such that the second notch is oriented transversely relative to a second height of the second thickness control securement member;
    a frame which is adjustably securable between the first thickness control securement member and the second thickness control securement member when a first portion of the frame is positioned within the first notch and a second portion of the frame is positioned within the second notch such that the frame is oriented transversely relative to the first and second heights such that the frame encompasses a wound or incision within the frame, and
    wherein the frame has a relaxed configuration and a biasing configuration which imparts a biasing force generated by the frame between the first and second thickness control securement members when in the biasing configuration such that the biasing force is applied at a distance from tissue to be approximated via the first and second fixation members.

16. The assembly of claim 15 further comprising one or more biasing members operably coupled to the first and second thickness control securement members.

17. The assembly of claim 15 wherein the frame is comprised of one or more segmented rod members.

18. The assembly of claim 15 wherein the frame is comprised a continuous material.

19. The assembly of claim 15 wherein the frame defines one or more bends.

20. The assembly of claim 15 wherein the first and second fixation members is each slidably adjustable through the first and second receiving channels respectively.

21. The assembly of claim 15 wherein the first and second portions of the frame are slidably positioned within the first and second receiving notches respectively.

22. The assembly of claim 15 further comprising a first anchor cup and a second anchor cup each sized to be positioned within a body lumen and each defining a portion for receiving a respective first tip of the first fixation member and a second tip of the second fixation member.

23. The assembly of claim 15 further comprising a handle removably securable to the first and second fixation members.

24. The assembly of claim 15 further comprising a protective covering or shell positionable over the tissue securement assembly.

25. A tissue securement assembly, comprising:
a fixation member having a length;
a thickness control securement member defining a receiving channel through which the fixation member is adjustably securable along the length, wherein the thickness control securement member further defines a receiving notch formed at least partially around a perimeter of the thickness control securement member such that the notch is oriented transversely relative to a height of the thickness control securement member;
a frame which is adjustably positionable relative to a wound or incision such that the frame at least partially surrounds the wound or incision and is oriented transversely relative to the height of the thickness control securement member and provides a frame biasing force generated by the frame;
a biasing member coupled between the frame and the thickness control securement member such that the biasing member provides a biasing force against the thickness control securement member at a distance from the wound or incision to be approximated.

26. The assembly of claim 25 further comprising:
a second fixation member having a second length;
a second thickness control securement member defining a second receiving channel through which the second fixation member is adjustably securable along the second length, wherein the second thickness control securement member further defines a second receiving notch formed at least partially around a second perimeter of the second thickness control securement member such that the second notch is oriented transversely relative to a second height of the second thickness control securement member; and
a second biasing member coupled between the frame and the second thickness control securement member when a second portion of the frame is positioned within the second notch such that the frame is oriented transversely relative to the first and second heights, where the second biasing member is coupled at a location opposite to the thickness control securement member such that a second biasing force is provided in a direction opposite to the biasing force.

27. The assembly of claim 25 further comprising an anchor positionable near or at a proximal end of the length of the fixation member.

28. The assembly of claim 25 wherein the frame comprises an elongate length and width which is sized to be positioned in parallel externally of a wound or incision.

29. The assembly of claim 25 wherein the frame is comprised of one or more segmented rod members.

30. The assembly of claim 25 wherein the frame is comprised a continuous material.

31. The assembly of claim 25 wherein the frame defines one or more bends.

32. The assembly of claim 25 further comprising an anchor cup sized to be positioned within a body lumen and defining a portion for receiving a tip of the fixation member.

33. The assembly of claim 25 further comprising a handle removably securable to the fixation member.

34. The assembly of claim 25 further comprising a protective covering or shell positionable over the tissue securement assembly.

* * * * *